US010335162B2

(12) United States Patent
Maxson

(10) Patent No.: US 10,335,162 B2
(45) Date of Patent: Jul. 2, 2019

(54) TIBIAL TUBERCLE OSTEOTOMY

(71) Applicant: Biomet Sports Medicine, LLC, Warsaw, IN (US)

(72) Inventor: William Maxson, Ponte Vedra, FL (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 80 days.

(21) Appl. No.: 15/800,399

(22) Filed: Nov. 1, 2017

(65) Prior Publication Data
US 2018/0049750 A1 Feb. 22, 2018

Related U.S. Application Data

(62) Division of application No. 14/500,019, filed on Sep. 29, 2014, now Pat. No. 9,833,245.

(51) Int. Cl.
*A61B 17/15* (2006.01)
*A61B 17/17* (2006.01)
*A61B 17/80* (2006.01)
*A61F 2/28* (2006.01)
*A61B 17/56* (2006.01)

(52) U.S. Cl.
CPC .......... *A61B 17/152* (2013.01); *A61B 17/151* (2013.01); *A61B 17/1764* (2013.01); *A61B 17/8095* (2013.01); *A61B 2017/568* (2013.01); *A61F 2002/2892* (2013.01)

(58) Field of Classification Search
CPC .............. A61B 17/15–154; A61B 17/17–1796
See application file for complete search history.

(56) References Cited

U.S. PATENT DOCUMENTS

| 1,480,285 | A | 1/1924 | Moore |
| 2,181,746 | A | 11/1939 | Siebrandt |
| 2,407,845 | A | 9/1946 | Orisan |
| 2,416,228 | A | 2/1947 | Sheppard |
| 2,618,913 | A | 11/1952 | Plancon et al. |

(Continued)

FOREIGN PATENT DOCUMENTS

| CA | 2447694 A1 | 12/2002 |
| CA | 2501041 A1 | 4/2004 |

(Continued)

OTHER PUBLICATIONS

"3D-Implantatplanung und StereolithographieImplantatbohrschablonen", Stomatologie 101.3, (2004), 55-59.

(Continued)

*Primary Examiner* — Eric S Gibson
(74) *Attorney, Agent, or Firm* — Schwegman Lundberg & Woessner, P.A.

(57) ABSTRACT

Patient-specific guides for a tibial tubercle osteotomy are provided. The guides include a guide body defining a portion with a bone-engaging surface that conforms as a negative surface to a corresponding surface of a specific patient's tibia, and a guide portion that guides a surgical instrument to a specific location on the specific patient's tibia, wherein the bone-engaging surface and guide portion are configured during a pre-operative planning stage. Methods for performing a tibial tubercle osteotomy with the patient-specific guides are also provided.

10 Claims, 6 Drawing Sheets

(56) References Cited

U.S. PATENT DOCUMENTS

| | | |
|---|---|---|
| 2,910,978 A | 11/1959 | Urist |
| 3,330,611 A | 7/1967 | Heifetz |
| 3,840,904 A | 10/1974 | Tronzo |
| 3,975,858 A | 8/1976 | Much |
| 4,246,895 A | 1/1981 | Rehder |
| 4,306,866 A | 12/1981 | Weissman |
| 4,324,006 A | 4/1982 | Charnley |
| 4,421,112 A | 12/1983 | Mains et al. |
| 4,436,684 A | 3/1984 | White |
| 4,457,306 A | 7/1984 | Borzone |
| 4,475,549 A | 10/1984 | Oh |
| 4,506,393 A | 3/1985 | Murphy |
| 4,524,766 A | 6/1985 | Petersen |
| 4,528,980 A | 7/1985 | Kenna |
| 4,565,191 A * | 1/1986 | Slocum .............. A61B 17/152 606/87 |
| 4,619,658 A | 10/1986 | Pappas et al. |
| 4,621,630 A | 11/1986 | Kenna |
| 4,632,111 A | 12/1986 | Roche |
| 4,633,862 A | 1/1987 | Petersen |
| 4,663,720 A | 5/1987 | Duret et al. |
| 4,677,973 A * | 7/1987 | Slocum ............. A61B 17/1637 606/60 |
| 4,689,984 A | 9/1987 | Kellner |
| 4,695,283 A | 9/1987 | Aldinger |
| 4,696,292 A | 9/1987 | Heiple |
| 4,703,751 A | 11/1987 | Pohl |
| 4,704,686 A | 11/1987 | Aldinger |
| 4,706,660 A | 11/1987 | Petersen |
| 4,719,907 A | 1/1988 | Banko et al. |
| 4,721,104 A | 1/1988 | Kaufman et al. |
| 4,722,330 A | 2/1988 | Russell et al. |
| 4,759,350 A | 7/1988 | Dunn et al. |
| 4,778,474 A | 10/1988 | Homsy |
| 4,800,874 A | 1/1989 | David et al. |
| 4,821,213 A | 4/1989 | Cline et al. |
| 4,822,365 A | 4/1989 | Walker et al. |
| 4,841,975 A | 6/1989 | Woolson |
| 4,846,161 A | 7/1989 | Roger |
| 4,871,975 A | 10/1989 | Nawata et al. |
| 4,892,545 A | 1/1990 | Day et al. |
| 4,893,619 A | 1/1990 | Dale et al. |
| 4,896,663 A | 1/1990 | Vandewalls |
| 4,907,577 A | 3/1990 | Wu |
| 4,927,422 A | 5/1990 | Engelhardt |
| 4,936,862 A | 6/1990 | Walker et al. |
| 4,952,213 A | 8/1990 | Bowman et al. |
| 4,959,066 A | 9/1990 | Dunn et al. |
| 4,976,737 A | 12/1990 | Leake |
| 4,979,949 A | 12/1990 | Matsen, III et al. |
| 4,985,037 A | 1/1991 | Petersen |
| 5,002,579 A | 3/1991 | Copf et al. |
| 5,006,121 A | 4/1991 | Hafeli |
| 5,007,936 A | 4/1991 | Woolson |
| 5,030,219 A | 7/1991 | Matsen et al. |
| 5,030,221 A | 7/1991 | Buechel et al. |
| 5,041,117 A | 8/1991 | Engelhardt |
| 5,053,037 A | 10/1991 | Lackey et al. |
| 5,053,039 A | 10/1991 | Hofmann et al. |
| 5,056,351 A | 10/1991 | Stiver et al. |
| 5,086,401 A | 2/1992 | Glassman et al. |
| 5,098,383 A | 3/1992 | Hemmy et al. |
| 5,098,436 A | 3/1992 | Ferrante et al. |
| 5,108,425 A | 4/1992 | Hwang |
| 5,122,144 A | 6/1992 | Bert et al. |
| 5,123,927 A | 6/1992 | Duncan et al. |
| 5,129,908 A | 7/1992 | Petersen |
| 5,129,909 A | 7/1992 | Sutherland |
| 5,133,760 A | 7/1992 | Petersen et al. |
| 5,140,777 A | 8/1992 | Ushiyama et al. |
| 5,150,304 A | 9/1992 | Berchem et al. |
| 5,176,684 A | 1/1993 | Ferrante et al. |
| 5,194,066 A | 3/1993 | Van Zile |
| 5,234,433 A | 8/1993 | Bert et al. |
| 5,246,444 A * | 9/1993 | Schreiber ............ A61B 17/152 606/87 |
| 5,253,506 A | 10/1993 | Davis et al. |
| 5,258,032 A | 11/1993 | Bertin |
| 5,261,915 A | 11/1993 | Durlacher et al. |
| 5,274,565 A | 12/1993 | Reuben |
| 5,282,802 A | 2/1994 | Mahony, III |
| 5,299,288 A | 3/1994 | Glassman et al. |
| 5,300,077 A | 4/1994 | Howell |
| 5,320,529 A | 6/1994 | Pompa |
| 5,320,625 A | 6/1994 | Bertin |
| 5,323,697 A | 6/1994 | Schrock |
| 5,342,366 A | 8/1994 | Whiteside et al. |
| 5,344,423 A | 9/1994 | Dietz et al. |
| 5,360,446 A | 11/1994 | Kennedy |
| 5,364,402 A | 11/1994 | Mumme et al. |
| 5,368,858 A | 11/1994 | Hunziker |
| 5,370,692 A | 12/1994 | Fink et al. |
| 5,370,699 A | 12/1994 | Hood et al. |
| 5,405,395 A | 4/1995 | Coates |
| 5,408,409 A | 4/1995 | Glassman et al. |
| 5,411,521 A | 5/1995 | Putnam et al. |
| 5,415,662 A | 5/1995 | Ferrante et al. |
| 5,417,694 A | 5/1995 | Marik et al. |
| 5,438,263 A | 8/1995 | Dworkin et al. |
| 5,440,496 A | 8/1995 | Andersson et al. |
| 5,448,489 A | 9/1995 | Reuben |
| 5,449,360 A | 9/1995 | Schreiber |
| 5,452,407 A | 9/1995 | Crook |
| 5,454,816 A | 10/1995 | Ashby |
| 5,462,550 A | 10/1995 | Dietz et al. |
| 5,472,415 A | 12/1995 | King et al. |
| 5,474,559 A | 12/1995 | Bertin et al. |
| 5,490,854 A | 2/1996 | Fisher et al. |
| 5,496,324 A | 3/1996 | Barnes |
| 5,507,833 A | 4/1996 | Bohn |
| 5,514,519 A | 5/1996 | Neckers |
| 5,520,695 A | 5/1996 | Luckman |
| 5,527,317 A | 6/1996 | Ashby et al. |
| 5,539,649 A | 7/1996 | Walsh et al. |
| 5,540,695 A | 7/1996 | Levy |
| 5,545,222 A | 8/1996 | Bonutti |
| 5,549,688 A | 8/1996 | Ries et al. |
| 5,554,190 A | 9/1996 | Draenert |
| 5,560,096 A | 10/1996 | Stephens |
| 5,571,110 A | 11/1996 | Matsen, III et al. |
| 5,578,037 A | 11/1996 | Sanders et al. |
| 5,593,411 A | 1/1997 | Stalcup et al. |
| 5,595,703 A | 1/1997 | Swaelens et al. |
| 5,601,565 A | 2/1997 | Huebner |
| 5,607,431 A | 3/1997 | Dudasik et al. |
| 5,611,802 A | 3/1997 | Samuelson et al. |
| 5,613,969 A | 3/1997 | Jenkins, Jr. |
| 5,620,448 A | 4/1997 | Puddu |
| 5,634,927 A | 6/1997 | Houston et al. |
| 5,641,323 A | 6/1997 | Caldarise |
| 5,653,714 A | 8/1997 | Dietz et al. |
| 5,658,294 A | 8/1997 | Sederholm |
| 5,662,656 A | 9/1997 | White |
| 5,662,710 A | 9/1997 | Bonutti |
| 5,671,018 A | 9/1997 | Ohara et al. |
| 5,676,668 A | 10/1997 | McCue et al. |
| 5,677,107 A | 10/1997 | Neckers |
| 5,681,354 A | 10/1997 | Eckhoff |
| 5,682,886 A | 11/1997 | Delp et al. |
| 5,683,469 A | 11/1997 | Johnson et al. |
| 5,690,635 A | 11/1997 | Matsen, III et al. |
| 5,697,933 A * | 12/1997 | Gundlapalli ....... A61B 17/1714 606/206 |
| 5,702,460 A | 12/1997 | Carls et al. |
| 5,702,464 A | 12/1997 | Lackey et al. |
| 5,704,941 A | 1/1998 | Jacober et al. |
| 5,709,689 A | 1/1998 | Ferrante et al. |
| 5,720,752 A | 2/1998 | Elliot et al. |
| 5,722,978 A | 3/1998 | Jenkins, Jr. |
| 5,725,376 A | 3/1998 | Poirier |
| 5,725,593 A | 3/1998 | Caracciolo |
| 5,735,277 A | 4/1998 | Schuster |
| 5,745,834 A | 4/1998 | Bampton et al. |

(56) References Cited

U.S. PATENT DOCUMENTS

| | | | |
|---|---|---|---|
| 5,748,767 A | 5/1998 | Raab | |
| 5,749,875 A | 5/1998 | Puddu | |
| 5,749,876 A | 5/1998 | Duvillier et al. | |
| 5,762,125 A | 6/1998 | Mastrorio | |
| 5,766,251 A | 6/1998 | Koshino | |
| 5,768,134 A | 6/1998 | Swaelens et al. | |
| 5,769,092 A | 6/1998 | Williamson, Jr. | |
| 5,776,200 A | 7/1998 | Johnson et al. | |
| 5,786,217 A | 7/1998 | Tubo et al. | |
| 5,792,143 A | 8/1998 | Samuelson et al. | |
| 5,798,924 A | 8/1998 | Eufinger et al. | |
| 5,799,055 A | 8/1998 | Peshkin et al. | |
| 5,824,083 A | 10/1998 | Draenert | |
| 5,835,619 A | 11/1998 | Morimoto et al. | |
| 5,843,085 A * | 12/1998 | Graser | A61B 17/15 606/87 |
| 5,860,980 A | 1/1999 | Axelson, Jr. et al. | |
| 5,860,981 A | 1/1999 | Bertin et al. | |
| 5,871,018 A | 2/1999 | Delp et al. | |
| 5,876,456 A | 3/1999 | Sederholm et al. | |
| 5,879,398 A | 3/1999 | Swarts et al. | |
| 5,879,402 A | 3/1999 | Lawes et al. | |
| 5,880,976 A | 3/1999 | DiGioia, III et al. | |
| 5,885,297 A | 3/1999 | Matsen | |
| 5,885,298 A | 3/1999 | Herrington et al. | |
| 5,888,219 A | 3/1999 | Bonutti | |
| 5,895,389 A | 4/1999 | Schenk et al. | |
| 5,899,907 A | 5/1999 | Johnson | |
| 5,901,060 A | 5/1999 | Schall et al. | |
| 5,911,724 A | 6/1999 | Wehrli | |
| 5,921,988 A | 7/1999 | Legrand | |
| 5,925,049 A | 7/1999 | Gustilo et al. | |
| 5,942,370 A | 8/1999 | Neckers | |
| 5,967,777 A | 10/1999 | Klein et al. | |
| 5,976,149 A | 11/1999 | Masini | |
| 5,980,526 A | 11/1999 | Johnson et al. | |
| 6,008,433 A * | 12/1999 | Stone | A61B 17/68 623/20.14 |
| 6,019,767 A | 2/2000 | Howell | |
| 6,033,415 A | 3/2000 | Mittelstadt et al. | |
| 6,042,612 A | 3/2000 | Voydeville | |
| 6,056,754 A | 5/2000 | Haines et al. | |
| 6,059,789 A | 5/2000 | Dinger | |
| 6,059,833 A | 5/2000 | Doets | |
| 6,066,175 A | 5/2000 | Henderson et al. | |
| 6,086,593 A | 7/2000 | Bonutti | |
| 6,099,531 A * | 8/2000 | Bonutti | A61B 17/562 606/87 |
| 6,120,510 A | 9/2000 | Albrektsson et al. | |
| 6,120,544 A | 9/2000 | Grundei et al. | |
| 6,126,690 A | 10/2000 | Ateshian et al. | |
| 6,126,692 A | 10/2000 | Robie et al. | |
| 6,136,033 A | 10/2000 | Suemer | |
| 6,156,069 A | 12/2000 | Amstutz | |
| 6,159,217 A | 12/2000 | Robie et al. | |
| 6,161,080 A | 12/2000 | Aouni-Ateshian et al. | |
| 6,162,257 A | 12/2000 | Gustilo et al. | |
| 6,187,010 B1 | 2/2001 | Masini | |
| 6,190,390 B1 * | 2/2001 | McAllister | A61B 17/1604 606/54 |
| 6,195,615 B1 | 2/2001 | Lysen | |
| 6,203,546 B1 * | 3/2001 | MacMahon | A61B 17/152 606/87 |
| 6,205,411 B1 | 3/2001 | Digioia, III et al. | |
| 6,206,927 B1 | 3/2001 | Fell et al. | |
| 6,210,445 B1 | 4/2001 | Zawadzki | |
| 6,238,435 B1 | 5/2001 | Meulink et al. | |
| 6,254,604 B1 | 7/2001 | Howell | |
| 6,258,097 B1 | 7/2001 | Cook et al. | |
| 6,264,698 B1 | 7/2001 | Lawes et al. | |
| 6,270,529 B1 | 8/2001 | Terrill-Grisoni et al. | |
| 6,273,891 B1 | 8/2001 | Masini | |
| 6,290,727 B1 | 9/2001 | Otto et al. | |
| 6,293,971 B1 | 9/2001 | Nelson et al. | |
| 6,302,913 B1 | 10/2001 | Ripamonti et al. | |
| 6,310,269 B1 | 10/2001 | Friese et al. | |
| 6,312,258 B1 | 11/2001 | Ashman | |
| 6,312,473 B1 | 11/2001 | Oshida | |
| 6,319,285 B1 | 11/2001 | Chamier et al. | |
| 6,322,728 B1 | 11/2001 | Brodkin et al. | |
| 6,325,829 B1 | 12/2001 | Schmotzer | |
| 6,327,491 B1 | 12/2001 | Franklin et al. | |
| 6,338,738 B1 | 1/2002 | Bellotti et al. | |
| 6,343,987 B2 | 2/2002 | Hayama et al. | |
| 6,354,011 B1 | 3/2002 | Albrecht | |
| 6,361,563 B2 | 3/2002 | Terrill-Grisoni et al. | |
| 6,379,299 B1 | 4/2002 | Borodulin et al. | |
| 6,379,388 B1 | 4/2002 | Ensign et al. | |
| 6,383,228 B1 | 5/2002 | Schmotzer | |
| 6,391,251 B1 | 5/2002 | Keicher et al. | |
| 6,395,005 B1 | 5/2002 | Lovell | |
| 6,423,061 B1 * | 7/2002 | Bryant | A61B 17/152 606/54 |
| 6,424,332 B1 | 7/2002 | Powell | |
| 6,427,698 B1 | 8/2002 | Yoon et al. | |
| 6,459,948 B1 | 10/2002 | Ateshian et al. | |
| 6,463,351 B1 | 10/2002 | Clynch | |
| 6,475,243 B1 | 11/2002 | Sheldon et al. | |
| 6,482,236 B2 | 11/2002 | Habecker | |
| 6,488,715 B1 | 12/2002 | Pope et al. | |
| 6,503,255 B1 | 1/2003 | Albrektsson et al. | |
| 6,508,980 B1 | 1/2003 | Sachs et al. | |
| 6,510,334 B1 | 1/2003 | Schuster et al. | |
| 6,514,259 B2 | 2/2003 | Picard et al. | |
| 6,517,583 B1 | 2/2003 | Pope et al. | |
| 6,519,998 B2 | 2/2003 | Ertl et al. | |
| 6,520,964 B2 | 2/2003 | Tallarida et al. | |
| 6,533,737 B1 | 3/2003 | Brosseau et al. | |
| 6,547,823 B2 | 4/2003 | Scarborough et al. | |
| 6,551,325 B2 | 4/2003 | Neubauer et al. | |
| 6,554,837 B1 | 4/2003 | Hauri et al. | |
| 6,556,008 B2 | 4/2003 | Thesen | |
| 6,558,391 B2 | 5/2003 | Axelson, Jr. et al. | |
| 6,558,428 B2 | 5/2003 | Park | |
| 6,562,073 B2 | 5/2003 | Foley | |
| 6,564,085 B2 | 5/2003 | Meaney et al. | |
| 6,567,681 B1 | 5/2003 | Lindequist | |
| 6,575,980 B1 | 6/2003 | Robie et al. | |
| 6,575,982 B1 | 6/2003 | Bonutti | |
| 6,591,581 B2 | 7/2003 | Schmieding | |
| 6,605,293 B1 | 8/2003 | Giordano et al. | |
| 6,610,067 B2 | 8/2003 | Tallarida et al. | |
| 6,622,567 B1 | 9/2003 | Hamel et al. | |
| 6,629,999 B1 | 10/2003 | Serafin, Jr. | |
| 6,641,617 B1 | 11/2003 | Merrill et al. | |
| 6,676,892 B2 | 1/2004 | Das et al. | |
| 6,682,566 B2 | 1/2004 | Draenert et al. | |
| 6,682,567 B1 | 1/2004 | Schroeder | |
| 6,696,073 B2 | 2/2004 | Boyce et al. | |
| 6,697,664 B2 | 2/2004 | Kienzle, III et al. | |
| 6,701,174 B1 | 3/2004 | Krause et al. | |
| 6,709,462 B2 | 3/2004 | Hanssen | |
| 6,711,431 B2 | 3/2004 | Sarin et al. | |
| 6,711,432 B1 | 3/2004 | Krause et al. | |
| 6,712,856 B1 | 3/2004 | Carignan et al. | |
| 6,716,249 B2 | 4/2004 | Hyde | |
| 6,725,077 B1 | 4/2004 | Balloni et al. | |
| 6,738,657 B1 | 5/2004 | Franklin et al. | |
| 6,740,092 B2 | 5/2004 | Lombardo et al. | |
| 6,749,638 B1 | 6/2004 | Saladino | |
| 6,750,653 B1 | 6/2004 | Zou et al. | |
| 6,772,026 B2 | 8/2004 | Bradbury et al. | |
| 6,780,190 B2 | 8/2004 | Maroney | |
| 6,786,930 B2 | 9/2004 | Biscup | |
| 6,799,066 B2 | 9/2004 | Steines et al. | |
| 6,823,871 B2 * | 11/2004 | Schmieding | A61B 17/1714 128/898 |
| 6,827,723 B2 | 12/2004 | Carson | |
| 6,887,247 B1 | 5/2005 | Couture et al. | |
| 6,905,514 B2 | 6/2005 | Carignan et al. | |
| 6,916,324 B2 | 7/2005 | Sanford et al. | |
| 6,923,817 B2 | 8/2005 | Carson et al. | |
| 6,923,831 B2 | 8/2005 | Fell et al. | |

(56) References Cited

U.S. PATENT DOCUMENTS

| | | |
|---|---|---|
| 6,932,842 B1 | 8/2005 | Litschko et al. |
| 6,942,475 B2 | 9/2005 | Ensign et al. |
| 6,944,518 B2 | 9/2005 | Roose |
| 6,945,976 B2 | 9/2005 | Ball et al. |
| 6,953,480 B2 | 10/2005 | Mears et al. |
| 6,960,216 B2 | 11/2005 | Kolb et al. |
| 6,975,755 B1 | 12/2005 | Baumberg |
| 6,990,220 B2 | 1/2006 | Ellis et al. |
| 6,993,406 B1 | 1/2006 | Cesarano, III et al. |
| 7,001,385 B2 | 2/2006 | Bonutti |
| 7,029,479 B2 | 4/2006 | Tallarida et al. |
| 7,042,222 B2 | 5/2006 | Zheng et al. |
| 7,048,741 B2 | 5/2006 | Swanson |
| 7,050,877 B2 | 5/2006 | Iseki et al. |
| 7,060,074 B2 | 6/2006 | Rosa et al. |
| 7,074,241 B2 | 7/2006 | Mckinnon |
| RE39,301 E | 9/2006 | Bertin |
| 7,104,997 B2 | 9/2006 | Lionberger et al. |
| 7,105,026 B2 | 9/2006 | Johnson et al. |
| 7,115,131 B2 | 10/2006 | Engh et al. |
| 7,121,832 B2 | 10/2006 | Hsieh et al. |
| 7,141,053 B2 | 11/2006 | Rosa et al. |
| D533,664 S | 12/2006 | Büttler et al. |
| 7,169,185 B2 | 1/2007 | Sidebotham |
| 7,174,282 B2 | 2/2007 | Hollister et al. |
| 7,176,466 B2 | 2/2007 | Rousso et al. |
| 7,184,814 B2 | 2/2007 | Lang et al. |
| 7,198,628 B2 | 4/2007 | Ondrla et al. |
| 7,218,232 B2 | 5/2007 | Disilvestro et al. |
| 7,239,908 B1 | 7/2007 | Alexander et al. |
| 7,241,315 B2 | 7/2007 | Evans |
| 7,255,702 B2 | 8/2007 | Serra et al. |
| 7,258,701 B2 | 8/2007 | Aram et al. |
| 7,275,218 B2 | 9/2007 | Petrella et al. |
| 7,282,054 B2 | 10/2007 | Steffensmeier et al. |
| 7,294,133 B2 | 11/2007 | Zink et al. |
| 7,297,164 B2 | 11/2007 | Johnson et al. |
| 7,309,339 B2 | 12/2007 | Cusick et al. |
| 7,333,013 B2 | 2/2008 | Berger |
| 7,335,231 B2 | 2/2008 | Mclean |
| 7,364,581 B2 * | 4/2008 | Michalowicz ....... A61B 17/157 606/87 |
| 7,371,260 B2 | 5/2008 | Malinin |
| 7,383,164 B2 | 6/2008 | Aram et al. |
| 7,385,498 B2 | 6/2008 | Dobosz |
| 7,388,972 B2 | 6/2008 | Kitson |
| 7,390,327 B2 | 6/2008 | Collazo et al. |
| 7,392,076 B2 | 6/2008 | Moctezuma De La Barrera |
| 7,427,200 B2 | 9/2008 | Noble et al. |
| 7,427,272 B2 | 9/2008 | Richard et al. |
| 7,468,075 B2 | 12/2008 | Lang et al. |
| 7,474,223 B2 | 1/2009 | Nycz et al. |
| 7,488,325 B2 | 2/2009 | Qian et al. |
| 7,494,510 B2 | 2/2009 | Zweymuller |
| 7,517,365 B2 | 4/2009 | Carignan et al. |
| 7,519,540 B2 | 4/2009 | Mayaud |
| 7,527,631 B2 | 5/2009 | Maroney et al. |
| 7,534,263 B2 | 5/2009 | Burdulis, Jr. et al. |
| 7,537,664 B2 | 5/2009 | O'neill et al. |
| 7,542,791 B2 | 6/2009 | Mire et al. |
| 7,559,931 B2 | 7/2009 | Stone |
| 7,575,602 B2 | 8/2009 | Amirouche et al. |
| 7,578,851 B2 | 8/2009 | Dong et al. |
| 7,582,091 B2 | 9/2009 | Duncan et al. |
| 7,591,821 B2 | 9/2009 | Kleman |
| 7,601,155 B2 | 10/2009 | Petersen |
| 7,603,192 B2 | 10/2009 | Martin et al. |
| 7,604,639 B2 | 10/2009 | Swanson |
| 7,611,516 B2 | 11/2009 | Maroney |
| 7,618,451 B2 | 11/2009 | Berez et al. |
| 7,621,915 B2 | 11/2009 | Frederick et al. |
| 7,625,409 B2 | 12/2009 | Saltzman et al. |
| 7,646,161 B2 | 1/2010 | Albu-schäffer et al. |
| 7,651,501 B2 | 1/2010 | Penenberg et al. |
| 7,670,345 B2 | 3/2010 | Plassky et al. |
| 7,682,398 B2 | 3/2010 | Croxton et al. |
| 7,695,477 B2 | 4/2010 | Creger et al. |
| 7,695,521 B2 | 4/2010 | Ely et al. |
| 7,699,847 B2 | 4/2010 | Sheldon et al. |
| 7,704,253 B2 | 4/2010 | Bastian et al. |
| 7,723,395 B2 | 5/2010 | Ringeisen et al. |
| 7,747,305 B2 | 6/2010 | Dean et al. |
| D622,854 S | 8/2010 | Otto et al. |
| 7,780,672 B2 | 8/2010 | Metzger et al. |
| 7,780,740 B2 | 8/2010 | Steinberg |
| 7,789,885 B2 | 9/2010 | Metzger |
| 7,794,466 B2 | 9/2010 | Merchant et al. |
| 7,794,467 B2 | 9/2010 | McGinley et al. |
| 7,794,504 B2 | 9/2010 | Case |
| 7,806,896 B1 | 10/2010 | Bonutti |
| 7,809,184 B2 | 10/2010 | Neubauer et al. |
| 7,819,925 B2 | 10/2010 | King et al. |
| 7,828,806 B2 | 11/2010 | Graf et al. |
| 7,833,245 B2 | 11/2010 | Kaes et al. |
| 7,837,690 B2 | 11/2010 | Metzger |
| 7,846,165 B2 * | 12/2010 | Aram ................... A61B 17/15 606/79 |
| 7,850,698 B2 | 12/2010 | Straszheim-Morley et al. |
| 7,879,109 B2 | 2/2011 | Borden et al. |
| 7,892,261 B2 | 2/2011 | Bonutti |
| 7,896,921 B2 | 3/2011 | Smith et al. |
| 7,926,363 B2 | 4/2011 | Miller et al. |
| 7,935,119 B2 * | 5/2011 | Ammann ............... A61B 17/15 606/87 |
| 7,935,150 B2 | 5/2011 | Carignan et al. |
| 7,938,861 B2 | 5/2011 | King et al. |
| 7,959,637 B2 | 6/2011 | Fox et al. |
| 7,962,196 B2 | 6/2011 | Tuma |
| 7,963,968 B2 | 6/2011 | Dees, Jr. |
| 7,967,823 B2 | 6/2011 | Ammann et al. |
| 7,967,868 B2 | 6/2011 | White et al. |
| 7,974,677 B2 | 7/2011 | Mire et al. |
| 7,981,158 B2 | 7/2011 | Fitz et al. |
| 7,988,736 B2 | 8/2011 | May et al. |
| 7,993,353 B2 | 8/2011 | Roßner et al. |
| 8,062,301 B2 | 11/2011 | Ammann et al. |
| 8,066,708 B2 | 11/2011 | Lang et al. |
| 8,070,752 B2 | 12/2011 | Metzger et al. |
| 8,083,745 B2 | 12/2011 | Lang et al. |
| 8,083,746 B2 | 12/2011 | Novak |
| 8,083,749 B2 | 12/2011 | Taber |
| 8,086,336 B2 | 12/2011 | Christensen |
| 8,092,465 B2 | 1/2012 | Metzger et al. |
| 8,105,330 B2 | 1/2012 | Fitz et al. |
| 8,122,582 B2 | 2/2012 | Burdulis, Jr. et al. |
| 8,133,230 B2 | 3/2012 | Stevens et al. |
| 8,133,234 B2 | 3/2012 | Meridew et al. |
| 8,137,406 B2 | 3/2012 | Novak et al. |
| 8,147,861 B2 | 4/2012 | Jones et al. |
| 8,160,345 B2 | 4/2012 | Pavlovskaia et al. |
| 8,167,951 B2 | 5/2012 | Ammann et al. |
| 8,170,641 B2 | 5/2012 | Belcher |
| 8,182,489 B2 | 5/2012 | Horacek |
| 8,192,441 B2 | 6/2012 | Collazo |
| 8,192,495 B2 | 6/2012 | Simpson et al. |
| 8,200,355 B2 | 6/2012 | Lee et al. |
| 8,211,112 B2 | 7/2012 | Novak et al. |
| 8,221,430 B2 | 7/2012 | Park et al. |
| 8,241,292 B2 * | 8/2012 | Collazo ................ A61B 17/152 606/87 |
| 8,241,293 B2 * | 8/2012 | Stone ................... A61B 17/151 606/87 |
| 8,246,680 B2 | 8/2012 | Betz et al. |
| 8,260,589 B1 | 9/2012 | Kumar |
| 8,265,790 B2 | 9/2012 | Amiot et al. |
| 8,268,099 B2 | 9/2012 | O'neill et al. |
| 8,268,100 B2 | 9/2012 | O'neill et al. |
| D669,176 S | 10/2012 | Frey |
| 8,282,646 B2 | 10/2012 | Schoenefeld et al. |
| 8,298,237 B2 | 10/2012 | Schoenefeld et al. |
| 8,303,596 B2 | 11/2012 | Plaßky et al. |
| 8,313,491 B2 | 11/2012 | Green, II et al. |
| D672,038 S | 12/2012 | Frey |
| 8,333,772 B2 | 12/2012 | Fox et al. |

(56) References Cited

U.S. PATENT DOCUMENTS

| | | |
|---|---|---|
| 8,337,503 B2 | 12/2012 | Lian |
| 8,355,773 B2 | 1/2013 | Leitner et al. |
| 8,372,078 B2 | 2/2013 | Collazo |
| 8,377,066 B2 | 2/2013 | Katrana et al. |
| 8,388,690 B2 | 3/2013 | Singhatat et al. |
| 8,398,646 B2 | 3/2013 | Metzger et al. |
| 8,407,067 B2 | 3/2013 | Uthgenannt et al. |
| 8,414,594 B2 | 4/2013 | Berger et al. |
| 8,419,741 B2 | 4/2013 | Carignan et al. |
| 8,425,522 B2 | 4/2013 | Bonutti |
| 8,430,882 B2 | 4/2013 | Lowry et al. |
| 8,430,931 B2 | 4/2013 | Acker et al. |
| 8,439,675 B2 | 5/2013 | De Moyer |
| 8,439,925 B2 | 5/2013 | Marino et al. |
| 8,444,564 B2 | 5/2013 | Mahfouz et al. |
| 8,444,651 B2 | 5/2013 | Kunz et al. |
| 8,457,930 B2 | 6/2013 | Schroeder |
| 8,460,302 B2 | 6/2013 | Park et al. |
| 8,469,961 B2 | 6/2013 | Alleyne et al. |
| 8,473,305 B2 | 6/2013 | Belcher et al. |
| 8,486,150 B2 | 7/2013 | White et al. |
| 8,500,740 B2 | 8/2013 | Bojarski et al. |
| 8,532,361 B2 | 9/2013 | Pavlovskaia et al. |
| 8,532,806 B1 | 9/2013 | Masson |
| 8,532,807 B2 | 9/2013 | Metzger |
| 8,535,387 B2 | 9/2013 | Meridew et al. |
| 8,543,234 B2 | 9/2013 | Gao |
| 8,545,508 B2 | 10/2013 | Collazo |
| 8,568,487 B2 | 10/2013 | Witt et al. |
| 8,591,516 B2 | 11/2013 | Metzger et al. |
| 8,597,365 B2 | 12/2013 | Meridew |
| 8,603,180 B2 | 12/2013 | White et al. |
| 8,608,748 B2 | 12/2013 | Metzger et al. |
| 8,608,749 B2 | 12/2013 | Meridew et al. |
| 8,617,170 B2 | 12/2013 | Ashby et al. |
| 8,617,174 B2 | 12/2013 | Axelson, Jr. et al. |
| 8,617,175 B2 | 12/2013 | Park et al. |
| 8,632,547 B2 * | 1/2014 | Maxson ............ A61B 17/151 606/88 |
| 8,652,142 B2 | 2/2014 | Geissler |
| 8,668,700 B2 | 3/2014 | Catanzarite et al. |
| 8,702,712 B2 | 4/2014 | Jordan et al. |
| 8,702,715 B2 | 4/2014 | Ammann et al. |
| 8,706,285 B2 | 4/2014 | Narainasamy et al. |
| 8,715,289 B2 | 5/2014 | Smith |
| 8,728,387 B2 | 5/2014 | Jones et al. |
| 8,735,773 B2 | 5/2014 | Lang |
| 8,764,760 B2 | 7/2014 | Metzger et al. |
| 8,771,279 B2 * | 7/2014 | Philippon ............ A61B 17/15 606/87 |
| 8,775,133 B2 | 7/2014 | Schroeder |
| 8,777,875 B2 | 7/2014 | Park |
| 8,828,016 B2 | 9/2014 | Major et al. |
| 8,828,087 B2 | 9/2014 | Stone et al. |
| 8,828,089 B1 | 9/2014 | Perez et al. |
| 8,834,568 B2 | 9/2014 | Shapiro |
| 8,858,561 B2 | 10/2014 | White et al. |
| 8,858,602 B2 * | 10/2014 | Weiner ............ A61B 17/151 606/282 |
| 8,864,769 B2 | 10/2014 | Stone et al. |
| 8,900,244 B2 | 12/2014 | Meridew et al. |
| 8,903,530 B2 | 12/2014 | Metzger |
| 8,926,618 B2 * | 1/2015 | Collazo ............ A61B 17/152 606/87 |
| 8,956,364 B2 | 2/2015 | Catanzarite |
| 8,979,936 B2 | 3/2015 | White et al. |
| 9,005,297 B2 | 4/2015 | Katrana et al. |
| 9,055,954 B2 * | 6/2015 | Aram ............ A61B 17/15 |
| 9,427,240 B2 * | 8/2016 | Von Zabern ......... A61B 17/151 |
| 9,833,245 B2 * | 12/2017 | Maxson ............ A61B 17/1764 |
| 2001/0005797 A1 | 6/2001 | Barlow et al. |
| 2001/0011190 A1 | 8/2001 | Park |
| 2001/0021876 A1 | 9/2001 | Terril-Grisoni et al. |
| 2001/0054478 A1 | 12/2001 | Watanabe et al. |
| 2002/0007294 A1 | 1/2002 | Bradbury et al. |
| 2002/0029045 A1 | 3/2002 | Bonutti |
| 2002/0052606 A1 | 5/2002 | Bonutti |
| 2002/0059049 A1 | 5/2002 | Bradbury et al. |
| 2002/0082741 A1 | 6/2002 | Mazumder et al. |
| 2002/0087274 A1 | 7/2002 | Alexander et al. |
| 2002/0092532 A1 | 7/2002 | Yoon |
| 2002/0107522 A1 | 8/2002 | Picard et al. |
| 2002/0128872 A1 | 9/2002 | Giammattei |
| 2002/0147415 A1 | 10/2002 | Martelli |
| 2002/0165552 A1 * | 11/2002 | Duffner ............ A61B 17/15 606/87 |
| 2002/0186818 A1 | 12/2002 | Arnaud et al. |
| 2002/0193797 A1 | 12/2002 | Johnson et al. |
| 2002/0198528 A1 | 12/2002 | Engh et al. |
| 2002/0198531 A1 | 12/2002 | Millard et al. |
| 2003/0009171 A1 | 1/2003 | Tornier |
| 2003/0009234 A1 | 1/2003 | Treacy et al. |
| 2003/0011624 A1 | 1/2003 | Ellis |
| 2003/0018338 A1 | 1/2003 | Axelson, Jr. et al. |
| 2003/0039676 A1 | 2/2003 | Boyce et al. |
| 2003/0055502 A1 | 3/2003 | Lang et al. |
| 2003/0105526 A1 * | 6/2003 | Bryant ............ A61F 2/28 623/16.11 |
| 2003/0109784 A1 | 6/2003 | Loh et al. |
| 2003/0120276 A1 | 6/2003 | Tallarida et al. |
| 2003/0130741 A1 | 7/2003 | McMinn |
| 2003/0139817 A1 | 7/2003 | Tuke et al. |
| 2003/0158606 A1 | 8/2003 | Coon et al. |
| 2003/0171757 A1 | 9/2003 | Coon et al. |
| 2003/0216669 A1 | 11/2003 | Lang et al. |
| 2004/0018144 A1 | 1/2004 | Briscoe |
| 2004/0030245 A1 | 2/2004 | Noble et al. |
| 2004/0054372 A1 | 3/2004 | Corden et al. |
| 2004/0054416 A1 | 3/2004 | Wyss et al. |
| 2004/0068187 A1 | 4/2004 | Krause et al. |
| 2004/0092932 A1 | 5/2004 | Aubin et al. |
| 2004/0098133 A1 | 5/2004 | Carignan et al. |
| 2004/0102852 A1 | 5/2004 | Johnson et al. |
| 2004/0102866 A1 | 5/2004 | Harris et al. |
| 2004/0106926 A1 | 6/2004 | Leitner et al. |
| 2004/0115586 A1 | 6/2004 | Andreiko et al. |
| 2004/0122436 A1 | 6/2004 | Grimm |
| 2004/0122439 A1 | 6/2004 | Dwyer et al. |
| 2004/0128026 A1 | 7/2004 | Harris et al. |
| 2004/0133276 A1 | 7/2004 | Lang et al. |
| 2004/0138754 A1 | 7/2004 | Lang et al. |
| 2004/0143336 A1 | 7/2004 | Burkinshaw |
| 2004/0147927 A1 | 7/2004 | Tsougarakis et al. |
| 2004/0148026 A1 | 7/2004 | Bonutti |
| 2004/0153079 A1 | 8/2004 | Tsougarakis et al. |
| 2004/0153087 A1 | 8/2004 | Sanford et al. |
| 2004/0158254 A1 | 8/2004 | Eisermann |
| 2004/0158255 A1 | 8/2004 | Justin et al. |
| 2004/0162619 A1 | 8/2004 | Blaylock et al. |
| 2004/0167390 A1 | 8/2004 | Alexander et al. |
| 2004/0171924 A1 | 9/2004 | Mire et al. |
| 2004/0172137 A1 | 9/2004 | Blaylock et al. |
| 2004/0181144 A1 | 9/2004 | Cinquin et al. |
| 2004/0193169 A1 | 9/2004 | Schon et al. |
| 2004/0204644 A1 | 10/2004 | Tsougarakis et al. |
| 2004/0204760 A1 | 10/2004 | Fitz et al. |
| 2004/0212586 A1 | 10/2004 | Trueman, III |
| 2004/0220583 A1 | 11/2004 | Pieczynski, II et al. |
| 2004/0236341 A1 | 11/2004 | Petersen |
| 2004/0236424 A1 | 11/2004 | Berez et al. |
| 2004/0243481 A1 | 12/2004 | Bradbury et al. |
| 2004/0254584 A1 | 12/2004 | Sarin et al. |
| 2004/0260301 A1 | 12/2004 | Lionberger et al. |
| 2005/0008887 A1 | 1/2005 | Haymann et al. |
| 2005/0010227 A1 | 1/2005 | Paul |
| 2005/0010300 A1 | 1/2005 | Disilvestro et al. |
| 2005/0015022 A1 | 1/2005 | Richard et al. |
| 2005/0019664 A1 | 1/2005 | Matsumoto |
| 2005/0027303 A1 | 2/2005 | Lionberger et al. |
| 2005/0027361 A1 | 2/2005 | Reiley |
| 2005/0043806 A1 | 2/2005 | Cook et al. |
| 2005/0043837 A1 | 2/2005 | Rubbert et al. |
| 2005/0049524 A1 | 3/2005 | Lefevre et al. |
| 2005/0049603 A1 | 3/2005 | Calton et al. |

(56) References Cited

U.S. PATENT DOCUMENTS

| | | |
|---|---|---|
| 2005/0059873 A1 | 3/2005 | Glozman et al. |
| 2005/0060040 A1 | 3/2005 | Auxepaules et al. |
| 2005/0065628 A1 | 3/2005 | Roose |
| 2005/0070897 A1 | 3/2005 | Petersen |
| 2005/0071015 A1 | 3/2005 | Sekel |
| 2005/0075641 A1 | 4/2005 | Singhatat et al. |
| 2005/0096535 A1 | 5/2005 | De La Barrera |
| 2005/0113841 A1 | 5/2005 | Sheldon et al. |
| 2005/0113846 A1 | 5/2005 | Carson |
| 2005/0119664 A1 | 6/2005 | Carignan et al. |
| 2005/0131662 A1 | 6/2005 | Ascenzi et al. |
| 2005/0137708 A1 | 6/2005 | Clark |
| 2005/0148843 A1 | 7/2005 | Roose |
| 2005/0149042 A1 | 7/2005 | Metzger |
| 2005/0169893 A1* | 8/2005 | Koblish ............... A61B 17/80 424/93.7 |
| 2005/0171545 A1 | 8/2005 | Walsh et al. |
| 2005/0177245 A1 | 8/2005 | Leatherbury et al. |
| 2005/0203536 A1 | 9/2005 | Laffargue et al. |
| 2005/0203540 A1 | 9/2005 | Broyles |
| 2005/0209597 A1 | 9/2005 | Long et al. |
| 2005/0209605 A1 | 9/2005 | Grimm et al. |
| 2005/0216023 A1* | 9/2005 | Aram ................... A61B 17/15 606/86 R |
| 2005/0216305 A1 | 9/2005 | Funderud |
| 2005/0222571 A1 | 10/2005 | Ryan |
| 2005/0222573 A1 | 10/2005 | Branch et al. |
| 2005/0228393 A1 | 10/2005 | Williams, III et al. |
| 2005/0234461 A1 | 10/2005 | Burdulis, Jr. et al. |
| 2005/0234465 A1 | 10/2005 | Mccombs et al. |
| 2005/0234468 A1 | 10/2005 | Carson |
| 2005/0240195 A1 | 10/2005 | Axelson, Jr. et al. |
| 2005/0240267 A1 | 10/2005 | Randall et al. |
| 2005/0244239 A1 | 11/2005 | Shimp |
| 2005/0245934 A1 | 11/2005 | Tuke et al. |
| 2005/0245936 A1 | 11/2005 | Tuke et al. |
| 2005/0251147 A1 | 11/2005 | Novak |
| 2005/0267353 A1 | 12/2005 | Marquart et al. |
| 2005/0267485 A1 | 12/2005 | Cordes et al. |
| 2005/0267584 A1 | 12/2005 | Burdulis, Jr. et al. |
| 2005/0273114 A1 | 12/2005 | Novak |
| 2005/0283252 A1 | 12/2005 | Coon et al. |
| 2005/0283253 A1 | 12/2005 | Coon et al. |
| 2006/0004284 A1 | 1/2006 | Grunschlager et al. |
| 2006/0015120 A1 | 1/2006 | Richard et al. |
| 2006/0030853 A1 | 2/2006 | Haines |
| 2006/0038520 A1 | 2/2006 | Negoro |
| 2006/0052725 A1 | 3/2006 | Santilli |
| 2006/0058803 A1 | 3/2006 | Cuckler et al. |
| 2006/0058884 A1 | 3/2006 | Aram et al. |
| 2006/0058886 A1 | 3/2006 | Wozencroft |
| 2006/0089621 A1 | 4/2006 | Fard |
| 2006/0093988 A1 | 5/2006 | Swaelens et al. |
| 2006/0094951 A1 | 5/2006 | Dean et al. |
| 2006/0095044 A1 | 5/2006 | Grady, Jr. et al. |
| 2006/0100832 A1 | 5/2006 | Bowman |
| 2006/0105011 A1 | 5/2006 | Sun et al. |
| 2006/0111722 A1 | 5/2006 | Bouadi |
| 2006/0122616 A1 | 6/2006 | Bennett et al. |
| 2006/0122618 A1 | 6/2006 | Claypool et al. |
| 2006/0136058 A1 | 6/2006 | Pietrzak |
| 2006/0142657 A1 | 6/2006 | Quaid et al. |
| 2006/0147332 A1 | 7/2006 | Jones et al. |
| 2006/0149283 A1 | 7/2006 | May et al. |
| 2006/0155380 A1 | 7/2006 | Clemow et al. |
| 2006/0161165 A1 | 7/2006 | Swanson et al. |
| 2006/0161167 A1 | 7/2006 | Myers et al. |
| 2006/0172263 A1 | 8/2006 | Quadling et al. |
| 2006/0178497 A1 | 8/2006 | Gevaert et al. |
| 2006/0184177 A1 | 8/2006 | Echeverri |
| 2006/0184250 A1 | 8/2006 | Bandoh et al. |
| 2006/0190086 A1 | 8/2006 | Clemow et al. |
| 2006/0192319 A1 | 8/2006 | Solar |
| 2006/0195111 A1 | 8/2006 | Couture |
| 2006/0195194 A1 | 8/2006 | Gunther |
| 2006/0195198 A1 | 8/2006 | James |
| 2006/0200158 A1 | 9/2006 | Farling et al. |
| 2006/0204932 A1 | 9/2006 | Haymann et al. |
| 2006/0210644 A1 | 9/2006 | Levin |
| 2006/0217808 A1 | 9/2006 | Novak |
| 2006/0235421 A1 | 10/2006 | Rosa et al. |
| 2006/0241635 A1 | 10/2006 | Stumpo et al. |
| 2006/0241636 A1 | 10/2006 | Novak et al. |
| 2006/0241775 A1 | 10/2006 | Buss |
| 2006/0241776 A1 | 10/2006 | Brown et al. |
| 2006/0271058 A1 | 11/2006 | Ashton et al. |
| 2006/0276796 A1 | 12/2006 | Creger et al. |
| 2006/0276797 A1 | 12/2006 | Botimer |
| 2006/0287733 A1 | 12/2006 | Bonutti |
| 2006/0287891 A1 | 12/2006 | Grasso et al. |
| 2006/0293681 A1 | 12/2006 | Claypool et al. |
| 2007/0015995 A1 | 1/2007 | Lang et al. |
| 2007/0016008 A1 | 1/2007 | Schoenefeld |
| 2007/0016209 A1 | 1/2007 | Ammann et al. |
| 2007/0027680 A1 | 2/2007 | Ashley et al. |
| 2007/0039205 A1 | 2/2007 | Erb et al. |
| 2007/0043582 A1 | 2/2007 | Peveto et al. |
| 2007/0066917 A1 | 3/2007 | Hodorek et al. |
| 2007/0073136 A1 | 3/2007 | Metzger |
| 2007/0073137 A1 | 3/2007 | Schoenefeld |
| 2007/0083214 A1 | 4/2007 | Duncan et al. |
| 2007/0083266 A1 | 4/2007 | Lang |
| 2007/0100258 A1 | 5/2007 | Shoham et al. |
| 2007/0100450 A1 | 5/2007 | Hodorek |
| 2007/0100462 A1 | 5/2007 | Lang et al. |
| 2007/0106299 A1 | 5/2007 | Manspeizer |
| 2007/0118055 A1 | 5/2007 | Mccombs |
| 2007/0118138 A1 | 5/2007 | Seo et al. |
| 2007/0118243 A1 | 5/2007 | Schroeder et al. |
| 2007/0129809 A1 | 6/2007 | Meridew et al. |
| 2007/0142914 A1 | 6/2007 | Jones et al. |
| 2007/0150068 A1 | 6/2007 | Dong et al. |
| 2007/0156066 A1 | 7/2007 | Mcginley et al. |
| 2007/0156171 A1 | 7/2007 | Lang et al. |
| 2007/0162038 A1 | 7/2007 | Tuke |
| 2007/0162039 A1 | 7/2007 | Wozencroft |
| 2007/0173946 A1 | 7/2007 | Bonutti |
| 2007/0173948 A1 | 7/2007 | Meridew et al. |
| 2007/0185498 A2 | 8/2007 | Lavallee |
| 2007/0191962 A1 | 8/2007 | Jones |
| 2007/0198022 A1 | 8/2007 | Lang et al. |
| 2007/0203430 A1 | 8/2007 | Lang et al. |
| 2007/0203605 A1 | 8/2007 | Melton et al. |
| 2007/0219639 A1 | 9/2007 | Otto et al. |
| 2007/0219640 A1 | 9/2007 | Steinberg |
| 2007/0224238 A1 | 9/2007 | Mansmann et al. |
| 2007/0226986 A1 | 10/2007 | Park et al. |
| 2007/0233121 A1 | 10/2007 | Carson et al. |
| 2007/0233136 A1 | 10/2007 | Wozencroft |
| 2007/0233140 A1 | 10/2007 | Metzger et al. |
| 2007/0233141 A1 | 10/2007 | Park et al. |
| 2007/0233269 A1 | 10/2007 | Steines et al. |
| 2007/0233272 A1 | 10/2007 | Boyce et al. |
| 2007/0238069 A1 | 10/2007 | Lovald et al. |
| 2007/0239282 A1 | 10/2007 | Caylor, III et al. |
| 2007/0239481 A1 | 10/2007 | Disilvestro et al. |
| 2007/0244487 A1 | 10/2007 | Ammann et al. |
| 2007/0250169 A1 | 10/2007 | Lang |
| 2007/0253617 A1 | 11/2007 | Arata et al. |
| 2007/0255288 A1 | 11/2007 | Mahfouz et al. |
| 2007/0255412 A1 | 11/2007 | Hajaj et al. |
| 2007/0262867 A1 | 11/2007 | Westrick et al. |
| 2007/0272747 A1 | 11/2007 | Woods et al. |
| 2007/0276224 A1 | 11/2007 | Lang et al. |
| 2007/0276400 A1 | 11/2007 | Moore et al. |
| 2007/0276501 A1 | 11/2007 | Betz et al. |
| 2007/0288029 A1 | 12/2007 | Justin et al. |
| 2007/0288030 A1 | 12/2007 | Metzger et al. |
| 2008/0009952 A1 | 1/2008 | Hodge |
| 2008/0015599 A1 | 1/2008 | D'alessio et al. |
| 2008/0015603 A1 | 1/2008 | Collazo |
| 2008/0015604 A1 | 1/2008 | Collazo |
| 2008/0015605 A1 | 1/2008 | Collazo |
| 2008/0021299 A1 | 1/2008 | Meulink |

(56) References Cited

U.S. PATENT DOCUMENTS

| | | |
|---|---|---|
| 2008/0021494 A1 | 1/2008 | Schmelzeisen-redeker et al. |
| 2008/0021567 A1 | 1/2008 | Meulink et al. |
| 2008/0027563 A1 | 1/2008 | Johnson et al. |
| 2008/0033442 A1 | 2/2008 | Amiot et al. |
| 2008/0039850 A1 | 2/2008 | Rowley et al. |
| 2008/0051799 A1 | 2/2008 | Bonutti et al. |
| 2008/0051910 A1 | 2/2008 | Kammerzell et al. |
| 2008/0058945 A1 | 3/2008 | Hajaj et al. |
| 2008/0058947 A1 | 3/2008 | Earl et al. |
| 2008/0062183 A1 | 3/2008 | Swaelens |
| 2008/0065225 A1 | 3/2008 | Wasielewski et al. |
| 2008/0094396 A1 | 4/2008 | Sabczynsdi et al. |
| 2008/0097451 A1 | 4/2008 | Chen et al. |
| 2008/0114370 A1 | 5/2008 | Schoenefeld |
| 2008/0133022 A1 | 6/2008 | Caylor |
| 2008/0140081 A1 | 6/2008 | Heavener et al. |
| 2008/0140209 A1 | 6/2008 | Iannotti et al. |
| 2008/0140213 A1 | 6/2008 | Ammann et al. |
| 2008/0146969 A1 | 6/2008 | Kurtz |
| 2008/0147072 A1 | 6/2008 | Park et al. |
| 2008/0147073 A1 | 6/2008 | Ammann et al. |
| 2008/0147074 A1 | 6/2008 | Ammann et al. |
| 2008/0154267 A1 | 6/2008 | Merchant et al. |
| 2008/0161815 A1 | 7/2008 | Schoenefeld et al. |
| 2008/0161816 A1 | 7/2008 | Stevens et al. |
| 2008/0172125 A1 | 7/2008 | Ek |
| 2008/0195099 A1 * | 8/2008 | Minas ................... A61B 17/02 606/70 |
| 2008/0195107 A1 | 8/2008 | Cuckler et al. |
| 2008/0195108 A1 | 8/2008 | Bhatnagar et al. |
| 2008/0195109 A1 | 8/2008 | Hunter et al. |
| 2008/0195216 A1 | 8/2008 | Philipp |
| 2008/0200926 A1 | 8/2008 | Verard et al. |
| 2008/0208200 A1 | 8/2008 | Crofford |
| 2008/0208353 A1 | 8/2008 | Kumar et al. |
| 2008/0215059 A1 | 9/2008 | Carignan et al. |
| 2008/0230422 A1 | 9/2008 | Pleil et al. |
| 2008/0234664 A1 | 9/2008 | May et al. |
| 2008/0234683 A1 | 9/2008 | May |
| 2008/0234685 A1 | 9/2008 | Gjerde |
| 2008/0234833 A1 | 9/2008 | Bandoh et al. |
| 2008/0243127 A1 | 10/2008 | Lang et al. |
| 2008/0243257 A1 * | 10/2008 | Taber ................... A61B 17/152 623/20.16 |
| 2008/0255674 A1 | 10/2008 | Rahaman et al. |
| 2008/0257363 A1 | 10/2008 | Schoenefeld et al. |
| 2008/0262500 A1 * | 10/2008 | Collazo ................ A61B 17/152 606/88 |
| 2008/0262624 A1 | 10/2008 | White et al. |
| 2008/0269596 A1 | 10/2008 | Revie et al. |
| 2008/0269906 A1 | 10/2008 | Iannotti et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287926 A1 | 11/2008 | Abou El |
| 2008/0287954 A1 | 11/2008 | Kunz et al. |
| 2008/0294170 A1 | 11/2008 | O'brien |
| 2008/0294266 A1 | 11/2008 | Steinberg |
| 2008/0300600 A1 | 12/2008 | Guelat et al. |
| 2008/0306485 A1 | 12/2008 | Coon et al. |
| 2008/0306558 A1 | 12/2008 | Hakki |
| 2008/0312659 A1 | 12/2008 | Metzger et al. |
| 2008/0319448 A1 | 12/2008 | Lavallee et al. |
| 2009/0012526 A1 | 1/2009 | Fletcher |
| 2009/0018546 A1 | 1/2009 | Daley |
| 2009/0018666 A1 | 1/2009 | Grundei et al. |
| 2009/0024131 A1 | 1/2009 | Metzger et al. |
| 2009/0024169 A1 | 1/2009 | Triplett et al. |
| 2009/0043556 A1 | 2/2009 | Axelson et al. |
| 2009/0048618 A1 | 2/2009 | Harrison et al. |
| 2009/0076371 A1 | 3/2009 | Lang et al. |
| 2009/0076512 A1 | 3/2009 | Ammann et al. |
| 2009/0076520 A1 | 3/2009 | Choi |
| 2009/0076555 A1 | 3/2009 | Lowry et al. |
| 2009/0082770 A1 | 3/2009 | Worner et al. |
| 2009/0082774 A1 | 3/2009 | Oti et al. |
| 2009/0087276 A1 | 4/2009 | Rose |
| 2009/0088674 A1 | 4/2009 | Caillouette et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0088865 A1 | 4/2009 | Brehm |
| 2009/0088866 A1 | 4/2009 | Case |
| 2009/0089034 A1 | 4/2009 | Penney et al. |
| 2009/0089081 A1 | 4/2009 | Haddad |
| 2009/0093815 A1 | 4/2009 | Fletcher et al. |
| 2009/0093816 A1 | 4/2009 | Roose et al. |
| 2009/0096613 A1 | 4/2009 | Westrick |
| 2009/0099567 A1 | 4/2009 | Zajac |
| 2009/0105837 A1 | 4/2009 | Lafosse et al. |
| 2009/0116621 A1 | 5/2009 | Yuan et al. |
| 2009/0118736 A1 | 5/2009 | Kreuzer |
| 2009/0118769 A1 | 5/2009 | Sixto, Jr. et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0149964 A1 | 6/2009 | May et al. |
| 2009/0149965 A1 | 6/2009 | Quaid |
| 2009/0149977 A1 | 6/2009 | Schendel |
| 2009/0151736 A1 | 6/2009 | Belcher et al. |
| 2009/0157083 A1 | 6/2009 | Park et al. |
| 2009/0163922 A1 | 6/2009 | Meridew et al. |
| 2009/0163923 A1 | 6/2009 | Flett et al. |
| 2009/0164024 A1 | 6/2009 | Rudan et al. |
| 2009/0177282 A1 | 7/2009 | Bureau et al. |
| 2009/0187193 A1 | 7/2009 | Maroney et al. |
| 2009/0209884 A1 | 8/2009 | Van Vorhis et al. |
| 2009/0209961 A1 | 8/2009 | Ferrante et al. |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228016 A1 | 9/2009 | Alvarez |
| 2009/0234360 A1 | 9/2009 | Alexander |
| 2009/0248044 A1 | 10/2009 | Amiot et al. |
| 2009/0250413 A1 | 10/2009 | Hoeppner |
| 2009/0254093 A1 | 10/2009 | White et al. |
| 2009/0254367 A1 | 10/2009 | Belcher et al. |
| 2009/0259312 A1 | 10/2009 | Shterling et al. |
| 2009/0270868 A1 | 10/2009 | Park et al. |
| 2009/0274350 A1 | 11/2009 | Pavlovskaia et al. |
| 2009/0287217 A1 | 11/2009 | Ammann et al. |
| 2009/0287309 A1 | 11/2009 | Walch et al. |
| 2009/0306676 A1 | 12/2009 | Lang et al. |
| 2009/0307893 A1 | 12/2009 | Burdulis, Jr. et al. |
| 2009/0318836 A1 | 12/2009 | Stone et al. |
| 2009/0318921 A1 | 12/2009 | White et al. |
| 2009/0318924 A1 * | 12/2009 | Helenbolt ............ A61B 17/151 606/88 |
| 2010/0010493 A1 | 1/2010 | Dower |
| 2010/0016984 A1 | 1/2010 | Trabish |
| 2010/0016986 A1 | 1/2010 | Trabish |
| 2010/0023015 A1 | 1/2010 | Park |
| 2010/0030231 A1 | 2/2010 | Revie et al. |
| 2010/0036404 A1 | 2/2010 | Yi et al. |
| 2010/0042105 A1 | 2/2010 | Park et al. |
| 2010/0049195 A1 | 2/2010 | Park et al. |
| 2010/0057088 A1 | 3/2010 | Shah |
| 2010/0076439 A1 | 3/2010 | Hatch |
| 2010/0076505 A1 | 3/2010 | Borja |
| 2010/0076563 A1 | 3/2010 | Otto et al. |
| 2010/0076571 A1 | 3/2010 | Hatch |
| 2010/0082034 A1 | 4/2010 | Remia |
| 2010/0082035 A1 | 4/2010 | Keefer |
| 2010/0082067 A1 | 4/2010 | Kondrashov |
| 2010/0087829 A1 * | 4/2010 | Metzger ................ A61B 17/15 606/96 |

(56) References Cited

U.S. PATENT DOCUMENTS

| | | |
|---|---|---|
| 2010/0094295 A1 | 4/2010 | Schnieders et al. |
| 2010/0105011 A1 | 4/2010 | Karkar et al. |
| 2010/0121334 A1 | 5/2010 | Couture et al. |
| 2010/0121335 A1 | 5/2010 | Penenberg et al. |
| 2010/0137869 A1 | 6/2010 | Borja et al. |
| 2010/0137924 A1 | 6/2010 | Tuke et al. |
| 2010/0145343 A1 | 6/2010 | Johnson et al. |
| 2010/0145344 A1 | 6/2010 | Jordan et al. |
| 2010/0152782 A1* | 6/2010 | Stone ............ A61B 17/151 606/280 |
| 2010/0160917 A1 | 6/2010 | Fitz et al. |
| 2010/0160919 A1 | 6/2010 | Axelson, Jr. et al. |
| 2010/0168752 A1 | 7/2010 | Edwards |
| 2010/0168754 A1 | 7/2010 | Fitz et al. |
| 2010/0168857 A1 | 7/2010 | Hatch |
| 2010/0168866 A1 | 7/2010 | Shih |
| 2010/0179663 A1 | 7/2010 | Steinberg |
| 2010/0185202 A1 | 7/2010 | Lester et al. |
| 2010/0191244 A1 | 7/2010 | White et al. |
| 2010/0198067 A1 | 8/2010 | Mahfouz et al. |
| 2010/0198224 A1 | 8/2010 | Metzger et al. |
| 2010/0212138 A1 | 8/2010 | Carroll et al. |
| 2010/0217109 A1 | 8/2010 | Belcher |
| 2010/0217270 A1 | 8/2010 | Polinski et al. |
| 2010/0217336 A1 | 8/2010 | Crawford et al. |
| 2010/0217338 A1 | 8/2010 | Carroll et al. |
| 2010/0217399 A1 | 8/2010 | Groh |
| 2010/0228257 A1 | 9/2010 | Bonutti |
| 2010/0249657 A1 | 9/2010 | Nycz et al. |
| 2010/0249796 A1 | 9/2010 | Nycz |
| 2010/0256649 A1 | 10/2010 | Capsal et al. |
| 2010/0262150 A1 | 10/2010 | Lian |
| 2010/0274253 A1 | 10/2010 | Ure |
| 2010/0281678 A1 | 11/2010 | Burdulis, Jr. et al. |
| 2010/0286700 A1 | 11/2010 | Snider et al. |
| 2010/0291401 A1 | 11/2010 | Medina et al. |
| 2010/0292743 A1 | 11/2010 | Singhal et al. |
| 2010/0298894 A1 | 11/2010 | Bojarski et al. |
| 2010/0305574 A1 | 12/2010 | Fitz et al. |
| 2010/0318088 A1 | 12/2010 | Warne et al. |
| 2010/0324692 A1 | 12/2010 | Uthgenannt et al. |
| 2011/0004317 A1 | 1/2011 | Hacking et al. |
| 2011/0008754 A1 | 1/2011 | Bassett et al. |
| 2011/0009869 A1 | 1/2011 | Marino et al. |
| 2011/0014081 A1 | 1/2011 | Jones et al. |
| 2011/0015636 A1 | 1/2011 | Katrana et al. |
| 2011/0015639 A1 | 1/2011 | Metzger et al. |
| 2011/0015752 A1 | 1/2011 | Meridew |
| 2011/0016690 A1 | 1/2011 | Narainasamy et al. |
| 2011/0022049 A1 | 1/2011 | Huebner et al. |
| 2011/0022174 A1 | 1/2011 | Holdstein et al. |
| 2011/0029088 A1 | 2/2011 | Rauscher et al. |
| 2011/0029091 A1 | 2/2011 | Bojarski et al. |
| 2011/0029093 A1 | 2/2011 | Bojarski |
| 2011/0029116 A1 | 2/2011 | Jordan et al. |
| 2011/0035012 A1 | 2/2011 | Linares |
| 2011/0040303 A1 | 2/2011 | Iannotti et al. |
| 2011/0040334 A1 | 2/2011 | Kaes et al. |
| 2011/0046735 A1 | 2/2011 | Metzger et al. |
| 2011/0054478 A1 | 3/2011 | Vanasse et al. |
| 2011/0054479 A1* | 3/2011 | Aram ............ A61B 17/15 606/87 |
| 2011/0066193 A1 | 3/2011 | Lang et al. |
| 2011/0066245 A1 | 3/2011 | Lang et al. |
| 2011/0071528 A1 | 3/2011 | Carson |
| 2011/0071529 A1 | 3/2011 | Carson |
| 2011/0071530 A1 | 3/2011 | Carson |
| 2011/0071532 A1 | 3/2011 | Carson |
| 2011/0071533 A1* | 3/2011 | Metzger ............ A61B 17/157 606/88 |
| 2011/0071581 A1 | 3/2011 | Lang et al. |
| 2011/0071802 A1 | 3/2011 | Bojarski et al. |
| 2011/0087332 A1 | 4/2011 | Bojarski et al. |
| 2011/0092804 A1 | 4/2011 | Schoenefeld et al. |
| 2011/0093086 A1 | 4/2011 | Witt et al. |
| 2011/0106093 A1 | 5/2011 | Romano et al. |
| 2011/0106254 A1 | 5/2011 | Abel et al. |
| 2011/0125264 A1 | 5/2011 | Bagga et al. |
| 2011/0125284 A1 | 5/2011 | Gabbrielli et al. |
| 2011/0130795 A1 | 6/2011 | Ball |
| 2011/0151027 A1 | 6/2011 | Clineff et al. |
| 2011/0151259 A1 | 6/2011 | Jarman-smith et al. |
| 2011/0153025 A1 | 6/2011 | Mcminn |
| 2011/0160736 A1 | 6/2011 | Meridew et al. |
| 2011/0160867 A1 | 6/2011 | Meridew et al. |
| 2011/0166578 A1* | 7/2011 | Stone ............ A61B 17/151 606/88 |
| 2011/0172672 A1* | 7/2011 | Dubeau ............ A61B 17/151 606/87 |
| 2011/0177590 A1 | 7/2011 | Clyne et al. |
| 2011/0184419 A1 | 7/2011 | Meridew et al. |
| 2011/0184526 A1 | 7/2011 | White et al. |
| 2011/0190899 A1 | 8/2011 | Pierce et al. |
| 2011/0190901 A1 | 8/2011 | Weissberg et al. |
| 2011/0213376 A1* | 9/2011 | Maxson ............ A61B 17/151 606/88 |
| 2011/0214279 A1 | 9/2011 | Park et al. |
| 2011/0218545 A1 | 9/2011 | Catanzarite et al. |
| 2011/0224674 A1 | 9/2011 | White et al. |
| 2011/0238071 A1 | 9/2011 | Fernandez-scoma |
| 2011/0245835 A1 | 10/2011 | Dodds et al. |
| 2011/0251617 A1 | 10/2011 | Ammann et al. |
| 2011/0257657 A1 | 10/2011 | Turner et al. |
| 2011/0269100 A1 | 11/2011 | Furrer et al. |
| 2011/0275032 A1 | 11/2011 | Tardieu et al. |
| 2011/0276145 A1 | 11/2011 | Carignan et al. |
| 2011/0282473 A1 | 11/2011 | Pavlovskaia et al. |
| 2011/0295887 A1 | 12/2011 | Palmese et al. |
| 2011/0313424 A1 | 12/2011 | Bono et al. |
| 2011/0319745 A1 | 12/2011 | Frey |
| 2012/0010619 A1 | 1/2012 | Barsoum |
| 2012/0010710 A1 | 1/2012 | Frigg |
| 2012/0010711 A1 | 1/2012 | Antonyshyn et al. |
| 2012/0029345 A1 | 2/2012 | Mahfouz et al. |
| 2012/0029520 A1 | 2/2012 | Lang et al. |
| 2012/0041445 A1* | 2/2012 | Roose ............ A61B 17/1746 606/96 |
| 2012/0041446 A1 | 2/2012 | Wong et al. |
| 2012/0041564 A1 | 2/2012 | Landon |
| 2012/0065640 A1 | 3/2012 | Metzger et al. |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0089595 A1 | 4/2012 | Jaecksch et al. |
| 2012/0101586 A1 | 4/2012 | Carson |
| 2012/0109137 A1 | 5/2012 | Iannotti et al. |
| 2012/0109138 A1 | 5/2012 | Meridew et al. |
| 2012/0109226 A1 | 5/2012 | Iannotti et al. |
| 2012/0116203 A1 | 5/2012 | Vancraen et al. |
| 2012/0123422 A1 | 5/2012 | Agnihotri et al. |
| 2012/0130382 A1* | 5/2012 | Iannotti ............ A61B 17/15 606/87 |
| 2012/0130383 A1* | 5/2012 | Budoff ............ A61B 17/152 606/87 |
| 2012/0136365 A1 | 5/2012 | Iannotti et al. |
| 2012/0141034 A1 | 6/2012 | Iannotti et al. |
| 2012/0143197 A1 | 6/2012 | Lang et al. |
| 2012/0143267 A1 | 6/2012 | Iannotti et al. |
| 2012/0150242 A1 | 6/2012 | Mannion |
| 2012/0158002 A1 | 6/2012 | Carignan et al. |
| 2012/0165954 A1 | 6/2012 | Nimal |
| 2012/0184962 A1 | 7/2012 | Merchant |
| 2012/0192401 A1 | 8/2012 | Pavlovskaia et al. |
| 2012/0197410 A1* | 8/2012 | Horan ............ A61B 17/68 623/20.32 |
| 2012/0209276 A1 | 8/2012 | Schuster |
| 2012/0215225 A1 | 8/2012 | Philippon et al. |
| 2012/0215310 A1 | 8/2012 | Sharp et al. |
| 2012/0221017 A1 | 8/2012 | Bonutti |
| 2012/0226283 A1 | 9/2012 | Meridew et al. |
| 2012/0232596 A1 | 9/2012 | Ribeiro |
| 2012/0245587 A1 | 9/2012 | Fang et al. |
| 2012/0259335 A1 | 10/2012 | Scifert et al. |
| 2012/0265208 A1 | 10/2012 | Smith |

(56) References Cited

U.S. PATENT DOCUMENTS

| | | |
|---|---|---|
| 2012/0271131 A1 | 10/2012 | Kling et al. |
| 2012/0271314 A1 | 10/2012 | Stemniski et al. |
| 2012/0271366 A1 | 10/2012 | Katrana et al. |
| 2012/0276509 A1 | 11/2012 | Iannotti et al. |
| 2012/0277751 A1 | 11/2012 | Catanzarite et al. |
| 2012/0289965 A1 | 11/2012 | Gelaude et al. |
| 2012/0296339 A1 | 11/2012 | Iannotti et al. |
| 2012/0303004 A1 | 11/2012 | Uthgenannt et al. |
| 2012/0303033 A1* | 11/2012 | Weiner ............... A61B 17/151 606/87 |
| 2012/0310364 A1 | 12/2012 | Li et al. |
| 2012/0310399 A1 | 12/2012 | Metzger |
| 2012/0316564 A1* | 12/2012 | Serbousek ......... A61B 17/1764 606/80 |
| 2012/0323246 A1 | 12/2012 | Catanzarite et al. |
| 2012/0323282 A1 | 12/2012 | Brianza et al. |
| 2012/0323323 A1 | 12/2012 | Vargas et al. |
| 2013/0001121 A1 | 1/2013 | Metzger |
| 2013/0006250 A1 | 1/2013 | Metzger et al. |
| 2013/0018483 A1 | 1/2013 | Li et al. |
| 2013/0030540 A1 | 1/2013 | Leibinger |
| 2013/0035766 A1 | 2/2013 | Meridew |
| 2013/0046310 A1 | 2/2013 | Ranawat et al. |
| 2013/0053854 A1 | 2/2013 | Schoenefeld et al. |
| 2013/0056912 A1 | 3/2013 | O'neill et al. |
| 2013/0060253 A1 | 3/2013 | Couture et al. |
| 2013/0072940 A1 | 3/2013 | Dawood et al. |
| 2013/0085500 A1 | 4/2013 | Meridew et al. |
| 2013/0085590 A1 | 4/2013 | Bryan et al. |
| 2013/0119579 A1 | 5/2013 | Iannotti et al. |
| 2013/0123850 A1 | 5/2013 | Schoenefeld et al. |
| 2013/0131681 A1 | 5/2013 | Katrana et al. |
| 2013/0144392 A1 | 6/2013 | Hughes |
| 2013/0197528 A1 | 8/2013 | Zakaria et al. |
| 2013/0197529 A1 | 8/2013 | Metzger |
| 2013/0197687 A1 | 8/2013 | Pavlovskaia et al. |
| 2013/0218163 A1 | 8/2013 | Frey |
| 2013/0245631 A1 | 9/2013 | Bettenga |
| 2013/0245801 A1 | 9/2013 | Schroeder |
| 2013/0261503 A1 | 10/2013 | Sherman |
| 2013/0264749 A1 | 10/2013 | Jones et al. |
| 2013/0268085 A1 | 10/2013 | Dong |
| 2013/0289730 A1 | 10/2013 | Gabriel et al. |
| 2013/0317511 A1 | 11/2013 | Bojarski et al. |
| 2013/0326878 A1 | 12/2013 | Boehm et al. |
| 2013/0338673 A1 | 12/2013 | Keppler |
| 2014/0005672 A1 | 1/2014 | Edwards et al. |
| 2014/0012266 A1 | 1/2014 | Bonin, Jr. et al. |
| 2014/0052270 A1 | 2/2014 | Witt et al. |
| 2014/0066937 A1 | 3/2014 | Wiebe, III et al. |
| 2014/0081275 A1* | 3/2014 | Metzger ............... A61B 17/157 606/88 |
| 2014/0081659 A1 | 3/2014 | Nawana et al. |
| 2014/0088724 A1 | 3/2014 | Meridew |
| 2014/0094816 A1 | 4/2014 | White et al. |
| 2014/0100578 A1 | 4/2014 | Metzger et al. |
| 2014/0107651 A1 | 4/2014 | Meridew et al. |
| 2014/0107654 A1 | 4/2014 | Kehres et al. |
| 2014/0107715 A1 | 4/2014 | Heilman et al. |
| 2014/0127211 A1 | 5/2014 | Geles et al. |
| 2014/0135775 A1* | 5/2014 | Maxson ............... A61B 17/151 606/88 |
| 2014/0163564 A1 | 6/2014 | Bollinger |
| 2014/0163565 A1 | 6/2014 | Bollinger |
| 2014/0172116 A1* | 6/2014 | Maxson ............ A61B 17/8095 623/23.53 |
| 2014/0180341 A1* | 6/2014 | Kang ................ A61B 17/8095 606/281 |
| 2014/0188119 A1 | 7/2014 | Catanzarite et al. |
| 2014/0208578 A1* | 7/2014 | Linderman ......... A61F 2/30756 29/592 |
| 2014/0222157 A1 | 8/2014 | Al Hares et al. |
| 2014/0243833 A1 | 8/2014 | Smith |
| 2014/0257304 A1 | 9/2014 | Eash |
| 2014/0257508 A1 | 9/2014 | Bojarski et al. |
| 2014/0276854 A1 | 9/2014 | Schoenefeld et al. |
| 2014/0276856 A1 | 9/2014 | Schoenefeld |
| 2014/0276870 A1 | 9/2014 | Eash |
| 2014/0276873 A1 | 9/2014 | Meridew et al. |
| 2014/0288562 A1* | 9/2014 | Von Zabern ......... A61B 17/151 606/88 |
| 2014/0303938 A1 | 10/2014 | Schoenefeld et al. |
| 2014/0303990 A1 | 10/2014 | Schoenefeld et al. |
| 2014/0309644 A1 | 10/2014 | Metzger et al. |
| 2014/0324058 A1* | 10/2014 | Metzger ............ A61B 17/1764 606/96 |
| 2014/0378979 A1 | 12/2014 | Stone et al. |
| 2015/0038974 A1* | 2/2015 | Harbison ........... A61B 17/1764 606/88 |
| 2015/0071885 A1* | 3/2015 | Saw ................ A61B 17/1764 424/93.7 |
| 2015/0088293 A1 | 3/2015 | Metzger |
| 2015/0305752 A1* | 10/2015 | Eash ................ A61B 17/157 606/82 |
| 2015/0335367 A1* | 11/2015 | Austin ............. A61B 17/8095 606/87 |
| 2016/0089166 A1* | 3/2016 | Maxson ........... A61B 17/1764 606/88 |

FOREIGN PATENT DOCUMENTS

| | | |
|---|---|---|
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2588907 A1 | 6/2006 |
| CA | 2590534 A1 | 6/2006 |
| CN | 1630495 A | 6/2005 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 102038553 A | 5/2011 |
| CN | 102335742 A | 2/2012 |
| CN | 107072672 A | 8/2017 |
| DE | 04219939 A1 | 12/1993 |
| DE | 4421153 A1 | 12/1995 |
| DE | 102009028503 A1 | 2/2011 |
| DE | 102011082902 A1 | 3/2012 |
| DE | 102012205820 A1 | 10/2012 |
| DE | 112010003901 T5 | 11/2012 |
| EP | 0114505 A1 | 8/1984 |
| EP | 0255797 A1 | 2/1988 |
| EP | 0326768 A2 | 8/1989 |
| EP | 0579868 A2 | 1/1994 |
| EP | 0591985 A1 | 4/1994 |
| EP | 0645984 A1 | 4/1995 |
| EP | 0650706 A1 | 5/1995 |
| EP | 0916324 A2 | 5/1999 |
| EP | 1321107 A1 | 6/2003 |
| EP | 1327424 A1 | 7/2003 |
| EP | 1437102 A1 | 7/2004 |
| EP | 01486900 A1 | 12/2004 |
| EP | 1634551 A2 | 3/2006 |
| EP | 1832239 A1 | 9/2007 |
| EP | 1852072 A2 | 11/2007 |
| EP | 2029061 A2 | 3/2009 |
| EP | 2168507 A2 | 3/2010 |
| EP | 2303146 A1 | 4/2011 |
| EP | 2303192 A1 | 4/2011 |
| EP | 2352445 A1 | 8/2011 |
| EP | 2396741 A1 | 12/2011 |
| EP | 2398381 A1 | 12/2011 |
| EP | 2403437 A2 | 1/2012 |
| EP | 2491873 A2 | 8/2012 |
| EP | 2502582 A1 | 9/2012 |
| EP | 2709568 A1 | 3/2014 |
| FR | 2659226 A1 | 9/1991 |
| FR | 2721195 A1 | 12/1995 |
| FR | 2768916 A1 | 4/1999 |

(56) References Cited

FOREIGN PATENT DOCUMENTS

| | | |
|---|---|---|
| FR | 2979817 A1 | 3/2013 |
| GB | 2094590 A | 9/1982 |
| GB | 2197790 A1 | 6/1988 |
| GB | 2442441 A | 4/2008 |
| GB | 2447702 A | 9/2008 |
| GB | 2483980 A | 3/2012 |
| GB | 2486390 A | 6/2012 |
| GB | 2490220 A | 10/2012 |
| GB | 2491526 A | 12/2012 |
| JP | 59157715 A | 9/1984 |
| JP | 60231208 A | 11/1985 |
| JP | 6233790 A | 8/1994 |
| JP | 2000245758 A | 9/2000 |
| JP | 2005218861 A | 8/2005 |
| JP | 2009514612 A | 4/2009 |
| JP | 2011505080 A | 2/2011 |
| JP | 2011527885 A | 11/2011 |
| KR | 20050072500 A | 7/2005 |
| KR | 20050084024 A | 8/2005 |
| RU | 2083179 C1 | 7/1997 |
| RU | 2113182 C1 | 6/1998 |
| RU | 2125835 C1 | 2/1999 |
| RU | 2138223 C1 | 9/1999 |
| RU | 2175534 C2 | 11/2001 |
| RU | 2187975 C1 | 8/2002 |
| RU | 2218242 C2 | 12/2003 |
| TW | 231755 A | 5/2005 |
| TW | 201114409 A | 5/2011 |
| WO | WO-8807840 A1 | 10/1988 |
| WO | WO-9107139 A1 | 5/1991 |
| WO | WO-9325157 A1 | 12/1993 |
| WO | WO-9528688 A1 | 10/1995 |
| WO | WO-9952473 A1 | 10/1999 |
| WO | WO-9959106 A1 | 11/1999 |
| WO | WO-0170142 A1 | 9/2001 |
| WO | WO-0184479 A1 | 11/2001 |
| WO | WO-0217821 A2 | 3/2002 |
| WO | WO-2002026145 A1 | 4/2002 |
| WO | WO-0236024 A1 | 5/2002 |
| WO | WO-02096268 A2 | 12/2002 |
| WO | WO-03051210 A2 | 6/2003 |
| WO | WO-03051211 A1 | 6/2003 |
| WO | WO-2004032806 A1 | 4/2004 |
| WO | WO-2004049981 A2 | 6/2004 |
| WO | WO-2004051301 A2 | 6/2004 |
| WO | WO-2004078069 A2 | 9/2004 |
| WO | WO-2005051233 A2 | 6/2005 |
| WO | WO-2005051239 A1 | 6/2005 |
| WO | WO-2005051240 A1 | 6/2005 |
| WO | WO-2005077039 A2 | 8/2005 |
| WO | WO-06060795 A1 | 6/2006 |
| WO | WO-2006058057 A2 | 6/2006 |
| WO | WO-2006092600 A1 | 9/2006 |
| WO | WO-2006127486 A2 | 11/2006 |
| WO | WO-2006134345 A1 | 12/2006 |
| WO | WO-2006136955 A1 | 12/2006 |
| WO | WO-07041375 A2 | 4/2007 |
| WO | WO-2007053572 A2 | 5/2007 |
| WO | WO-2007062079 A2 | 5/2007 |
| WO | WO-2007092841 A2 | 8/2007 |
| WO | WO-2007137327 A1 | 12/2007 |
| WO | WO-2007145937 A2 | 12/2007 |
| WO | WO-2008014618 A1 | 2/2008 |
| WO | WO-2008021494 A2 | 2/2008 |
| WO | WO-2008040961 A1 | 4/2008 |
| WO | WO-2008044055 A1 | 4/2008 |
| WO | WO-2008091358 A1 | 7/2008 |
| WO | WO-2008101090 A2 | 8/2008 |
| WO | WO-2008109751 A1 | 9/2008 |
| WO | WO-2008112996 A1 | 9/2008 |
| WO | WO-2008140748 A1 | 11/2008 |
| WO | WO-2009001083 A1 | 12/2008 |
| WO | WO-2009001109 A1 | 12/2008 |
| WO | WO-2009025783 A1 | 2/2009 |
| WO | WO-2009073781 A2 | 6/2009 |
| WO | WO-2009129063 A1 | 10/2009 |
| WO | WO-2009129067 A1 | 10/2009 |
| WO | WO-2010033431 A1 | 3/2010 |
| WO | WO-2010093902 A1 | 8/2010 |
| WO | WO-2010096553 A1 | 8/2010 |
| WO | WO-2010096557 A2 | 8/2010 |
| WO | WO-2010124164 A1 | 10/2010 |
| WO | WO-2010129870 A1 | 11/2010 |
| WO | WO-2010144705 A1 | 12/2010 |
| WO | WO-2010148103 A1 | 12/2010 |
| WO | WO-2010150223 A1 | 12/2010 |
| WO | WO-2011018458 A1 | 2/2011 |
| WO | WO-2011019797 A3 | 2/2011 |
| WO | WO-2011041398 A1 | 4/2011 |
| WO | WO-2011060536 A1 | 5/2011 |
| WO | WO-2011080260 A1 | 7/2011 |
| WO | WO-2011106711 A1 | 9/2011 |
| WO | WO-2011109260 A1 | 9/2011 |
| WO | WO-2011110374 A1 | 9/2011 |
| WO | WO-2011117644 A2 | 9/2011 |
| WO | WO-2012006444 A2 | 1/2012 |
| WO | WO-2012033821 A1 | 3/2012 |
| WO | WO-2012058344 A1 | 5/2012 |
| WO | WO-2012058349 A4 | 5/2012 |
| WO | WO-2012058353 A4 | 5/2012 |
| WO | WO-2012058355 A4 | 5/2012 |
| WO | WO-2012061042 A1 | 5/2012 |
| WO | WO-2012116206 A1 | 8/2012 |
| WO | WO-2012158917 A1 | 11/2012 |
| WO | WO-2012173929 A1 | 12/2012 |
| WO | WO-2012174008 A1 | 12/2012 |
| WO | WO-2013179142 A1 | 12/2013 |
| WO | WO-2016053843 A1 | 4/2016 |

OTHER PUBLICATIONS

"Amazing Precision. Beautiful Results. The next evolution of MAKOplasty® is here", MAKO Surgical Corp., (Feb. 2009), 6 pgs.
"U.S. Appl. No. 14/500,019, Non Final Office Action dated Apr. 18, 2017", 19 pgs.
"U.S. Appl. No. 14/500,019, Notice of Allowance dated Aug. 4, 2017", 9 pgs.
"U.S. Appl. No, 14/500,019, Response filed Jun. 30, 2017 to Non Final Office Action dated Apr. 18, 2017", 13 pgs.
"Ascent Total Knee System", Biomet, Inc., (Oct. 31, 1999), 16 pgs.
"Australian Application Serial No. 2013222609, First Examiner Report dated Feb. 16, 2015", 5 pgs.
"Comprehensive® Reverse Shoulder System", Biomet Orthopedics brochure, (2009), 8 pgs.
"Comprehensive® Reverse Shoulder System Surgical Technique", Biomet Orthopedics, (2009-2012), 48 pgs.
"Comprehensive® Reverse Shoulder System Technical Design Features", Biomet Orthopedics, (2009), 3 pgs.
"Comprehensive® Shoulder System Surgical Technique", Biomet Orthopedics brochure, (2007), 1-53.
"Comprehensive® Total Shoulder System", Biomet Orthopedics brochure, (2011), 4 pgs.
"Customized Patient Instruments, Patient specific instruments for patient specific needs", DePuy Orthopaedics, Inc., (2008), 14 pgs.
"Customized Patient Instruments, Primary Cruciate Retaining Surgical Technique for use with the Sigma® Knee System Utilizing Specialist® 2 Instrumentation", DePuy Orthopaedics, Inc., (2008), 1-23.
"Discovery® Elbow System", Biomet Orthopedics, Inc., (Nov. 30, 2007), 3 pgs.
"Discovery® Elbow System Surgical Technique", Biomet Orthopedics, Inc., (Dec. 31, 2008), 1-25.
"European Application Serial No. 07809326.7, Examination Notification Art. 94(3) dated Jan. 22, 2015", 6 pgs.
"European Application Serial No. 07809326.7, Extended European Search Report dated Nov. 15, 2011", 6 pgs.
"European Application Serial No. 09731923.0, Examination Notification Art. 94(3) dated Feb. 10, 2015", 7 pgs.
"European Application Serial No. 10705064.3, Examination Notification Art. 94(3) dated Feb. 4, 2015", 6 pgs.

(56) References Cited

OTHER PUBLICATIONS

"European Application Serial No. 12724475.4, Examination Notification Art. 94(3) dated Nov. 24, 2014", 7 pgs.
"Great Britain Application Serial No. 1116054.6, Search Report dated Dec. 21, 2011", 4 pgs.
"Hipsextant Instructions of Use", Surgical Planning Associates, Inc., (2011), 19 pgs.
"International Application Serial No. PCT/EP2010/061630, International Search Report dated Nov. 30, 2010", 3 pgs.
"International Application Serial No. PCT/US2007/013223, International Preliminary Report on Patentability dated Dec. 24, 2008", 5 pgs.
"International Application Serial No. PCT/US2007/013223, International Search Report dated Nov. 26, 2007", 3 pgs.
"International Application Serial No. PCT/US2007/013223, Written Opinion dated Nov. 26, 2007", 4 pgs.
"International Application Serial No. PCT/US2009/039507, International Preliminary Report on Patentability dated Oct. 28, 2010", 9 pgs.
"International Application Serial No. PCT/US2009/039507, International Search Report dated Jul. 14, 2009", 6 pgs.
"International Application Serial No. PCT/US2009/039507, Written Opinion dated Jul. 14, 2009", 7 pgs.
"International Application Serial No. PCT/US2009/039578, International Preliminary Report on Patentability dated Oct. 28, 2010", 9 pgs.
"International Application Serial No. PCT/US2009/039578, International Search Report dated Jul. 31, 2009", 6 pgs.
"International Application Serial No. PCT/US2009/039578, Written Opinion dated Jul. 31, 2009", 7 pgs.
"International Application Serial No. PCT/US2009/056670, International Preliminary Report on Patentability dated Mar. 31, 2011", 12 pgs.
"International Application Serial No. PCT/US2009/056670, International Search Report dated Mar. 2, 2010", 7 pgs.
"International Application Serial No. PCT/US2009/056670, Invitation to Pay Additional Fees and Partial Search Report dated Nov. 26, 2009".
"International Application Serial No. PCT/US2009/056670, Written Opinion dated Mar. 2, 2010", 10 pgs.
"International Application Serial No. PCT/US2010/024073, International Preliminary Report on Patentability dated Aug. 25, 2011", 8 pgs.
"International Application Serial No. PCT/US2010/024073, International Search Report dated Jun. 4, 2010", 4 pgs.
"International Application Serial No. PCT/US2010/024073, Written Opinion dated Jun. 4, 2010", 6 pgs.
"International Application Serial No. PCT/US2010/024579, International Preliminary Report on Patentability dated Sep. 1, 2011", 7 pgs.
"International Application Serial No. PCT/US2010/024579, International Search Report dated Apr. 22, 2010", 3 pgs.
"International Application Serial No. PCT/US2010/024579, Written Opinion dated Apr. 22, 2010", 5 pgs.
"International Application Serial No. PCT/US2010/024584, International Preliminary Report on Patentability dated Sep. 1, 2011", 8 pgs.
"International Application Serial No. PCT/US2010/024584, International Search Report dated Aug. 19, 2010", 6 pgs.
"International Application Serial No. PCT/US2010/024584, Written Opinion dated Aug. 19, 2010", 6 pgs.
"International Application Serial No. PCT/US2010/038177, International Preliminary Report on Patentability dated Dec. 22, 2011", 10 pgs.
"International Application Serial No. PCT/US2010/038177, International Search Report dated Aug. 24, 2010", 4 pgs.
"International Application Serial No. PCT/US2010/038177, Written Opinion dated Aug. 24, 2010", 8 pgs.
"International Application Serial No. PCT/US2010/038845, International Preliminary Report on Patentability dated Jan. 5, 2012", 9 pgs.
"International Application Serial No. PCT/US2010/038845, International Search Report dated Oct. 5, 2010", 4 pgs.
"International Application Serial No. PCT/US2010/038845, Written Opinion dated Oct. 5, 2010", 7 pgs.
"International Application Serial No. PCT/US2010/050701, International Preliminary Report on Patentability dated Apr. 12, 2012", 10 pgs.
"International Application Serial No. PCT/US2010/050701, International Search Report dated Dec. 7, 2010", 6 pgs.
"International Application Serial No. PCT/US2010/050701, Written Opinion dated Dec. 7, 2010", 8 pgs.
"International Application Serial No. PCT/US2011/026333, International Preliminary Report on Patentability dated Sep. 7, 2012", 10 pgs.
"International Application Serial No. PCT/US2011/026333, International Search Report dated Aug. 9, 2011", 6 pgs.
"International Application Serial No. PCT/US2011/026333, Invitation to Pay Additional Fees dated May 3, 2011".
"International Application Serial No. PCT/US2011/026333, Written Opinion dated Aug. 9, 2011", 8 pgs.
"International Application Serial No. PCT/US2011/026412, International Search Report dated May 9, 2011", 5 pgs.
"International Application Serial No. PCT/US2011/026412, Written Opinion dated May 9, 2011", 6 pgs.
"International Application Serial No. PCT/US2011/057300, International Search Report dated Mar. 5, 2012", 7 pgs.
"International Application Serial No. PCT/US2011/057300, Written Opinion dated Mar. 5, 2012", 9 pgs.
"International Application Serial No. PCT/US2012/026356, International Preliminary Report on Patentability dated Sep. 6, 2013", 8 pgs.
"International Application Serial No. PCT/US2012/026356, International Search Report dated May 8, 2012", 5 pgs.
"International Application Serial No. PCT/US2012/026356, Written Opinion dated May 8, 2012", 6 pgs.
"International Application Serial No. PCT/US2012/038351, International Preliminary Report on Patentability dated Nov. 28, 2013", 9 pgs
"International Application Serial No. PCT/US2012/038351, Written Opinion dated Jul. 6, 2012", 8 pgs.
"International Application Serial No. PCT/US2012/041893, International Search Report dated Oct. 23, 2012", 5 pgs.
"International Application Serial No. PCT/US2012/042081, International Preliminary Report on Patentability dated Jan. 3, 2014", 7 pgs.
"International Application Serial No. PCT/US2012/042081, Written Opinion dated Sep. 5, 2012", 6 pgs.
"International Application Serial No. PCT/US2012/052853, International Preliminary Report on Patentability dated Mar. 13, 2014", 14 pgs.
"International Application Serial No. PCT/US2012/052853, International Search Report dated Nov. 15, 2012", 6 pgs.
"International Application Serial No. PCT/US2012/052853, Written Opinion dated Nov. 15, 2012", 12 pgs.
"International Application Serial No. PCT/US2012/059189, International Preliminary Report on Patentability dated Apr. 24, 2014", 10 pgs.
"International Application Serial No. PCT/US2012/059189, International Search Report dated Dec. 18, 2012", 6 pgs.
"International Application Serial No. PCT/US2012/059189, Written Opinion dated Dec. 18, 2012", 9 pgs.
"International Application Serial No. PCT/US2012/060842, International Preliminary Report on Patentability dated May 8, 2014", 7 pgs.
"International Application Serial No. PCT/US2012/060842, International Search Report dated Feb. 6, 2013", 4 pgs.
"International Application Serial No. PCT/US2012/060842, Written Opinion dated Feb. 6, 2013", 5 pgs.

(56) References Cited

OTHER PUBLICATIONS

"International Application Serial No. PCT/US2012/060848, International Preliminary Report on Patentability dated May 8, 2014", 11 pgs.
"International Application Serial No. PCT/US2012/060848, Invitation to Pay Additional Fees dated Feb. 6, 2013".
"International Application Serial No. PCT/US2012/060848, Written Opinion dated Apr. 12, 2013", 9 pgs.
"International Application Serial No. PCT/US2012/060853, International Preliminary Report on Patentability dated May 8, 2014", 11 pgs.
"International Application Serial No. PCT/US2012/060853, Invitation to Pay Additional Fees dated Feb. 7, 2013", 4 pgs.
"International Application Serial No. PCT/US2012/060853, Written Opinion dated Apr. 9, 2013", 9 pgs.
"International Application Serial No. PCT/US2012/060854, International Preliminary Report on Patentability dated May 8, 2014", 8 pgs.
"International Application Serial No. PCT/US2012/060854, International Search Report dated Feb. 6, 2013", 4 pgs.
"International Application Serial No. PCT/US2012/060854, Written Opinion dated Feb. 6, 2013", 6 pgs.
"International Application Serial No. PCT/US2013/026875, International Preliminary Report on Patentability dated Sep. 4, 2014", 9 pgs.
"International Application Serial No. PCT/US2013/026875, International Search Report dated Jun. 7, 2013", 5 pgs.
"International Application Serial No. PCT/US2013/026875, Written Opinion dated Jun. 7, 2013", 8 pgs.
"International Application Serial No. PCT/US2013/057097, International Preliminary Report on Patentability dated Mar. 12, 2015", 10 pgs.
"International Application Serial No. PCT/US2013/057097, International Search Report dated Oct. 14, 2013", 6 pgs.
"International Application Serial No. PCT/US2013/057097, Written Opinion dated Oct. 14, 2013", 9 pgs.
"International Application Serial No. PCT/US2013/067505, International Search Report dated Apr. 14, 2014", 5 pgs.
"International Application Serial No. PCT/US2013/067505, Invitation to Pay Additional Fees dated Feb. 6, 2014", 6 pgs.
"International Application Serial No. PCT/US2013/067505, Written Opinion dated Apr. 14, 2014", 11 pgs.
"International Application Serial No. PCT/US2013/074288, International Search Report dated May 23, 2014", 7 pgs.
"International Application Serial No. PCT/US2013/074288, Written Opinion dated May 23, 2014", 11 pgs.
"International Application Serial No. PCT/US2014/022000, International Search Report dated Jun. 24, 2014", 3 pgs.
"International Application Serial No. PCT/US2014/022000, Written Opinion dated Jun. 24, 2014", 5 pgs.
"International Application Serial No. PCT/US2014/023655, International Search Report dated Jul. 10, 2014", 4 pgs.
"International Application Serial No. PCT/US2014/023655, Written Opinion dated Jul. 10, 2014", 6 pgs.
"International Application Serial No. PCT/US2015/052591, International Preliminary Report on Patentability dated Apr. 13, 2017", 9 pgs.
"International Application Serial No. PCT/US2015/052591, International Search Report dated Mar. 3, 2016", 8 pgs.
"International Application Serial No. PCT/US2015/052591, Written Opinion dated Mar. 3, 2016", 7 pgs
"Is Subchondroplasty® Right for Me?", [Online] retrieved from the internet: <http://www.subchondroplast}'..com/about subchondroplast}'./is subchondroplasty right for >, (Jul. 1, 2013), 1 pg.
"Japanese Application Serial No. 2014511538, Office Action dated Apr. 7, 2015", (W/ English Translation), 8 pgs.
"Knee tensor combined with laser femoral head locator", Research Disclosure, No. 507, (Jul. 2006), 903.
"Method for constructing an allograft sleeve", Research Disclosure, No. 476, (Dec. 2003), 1294.

"OSS™ Orthopaedic Salvage System, Femoral/Tibial Augmentation", Biomet Orthopedics, Inc.,, (Mar. 31, 2004), 1-8.
"Oxford® Partial Knee", Biomet, (Feb. 2011), 8 pgs.
"Oxford® Partial Knee Microplasty® Instrumentation Surgical Technique", Biomet, (May 2011), 1-54.
"Patient Matched PMI Implants, C.A.M.R.A. 3-D Imaging", Brochure, Biomet, Inc., Form Y-BMI-191/013191, (1991), 6 pgs.
"Regenerex® Porous Titanium Construct", Biomet brochure, (2011), 12 pgs.
"Regenerex® Tibial Cone Augment, Surgical Technique Addendum to the Vanguard® SSK Revision System", brochure. Biomet® Orthopedics., (Mar. 31, 2010), 1-8.
"Signature™ Hip Technology Personalized Patient Care brochure", Biomet® Orthopedics., (2013), 8 pgs.
"Signature™ Personalized Patient Care", Surgical Technique Acetabular Guide System brochure, Biomet® Orthopedics, (2013), 1-13.
"Signature™ Personalized Patient Care, Surgical Technique Addendum to the Vanguard Knee System", Biomet® Orthopedics Brochure, (May 15, 2009), 1-8.
"Signature™ Personalized Patient Care, Surgical Technique Addendum Vanguard® Complete Knee System", Biomet® Orthopedics Brochure, (2011), 1-32.
"Subchondroplasty", [Online] retrieved from the internet: <http://www.subchondroplasty.com/>, (Jul. 1, 2013), 1 pg.
"The Oxford® Partial Knee Surgical Technique", Biomet, (Feb. 2010), 1-38.
"TruMatch™ Personalized knee replacement solutions", SIGMA® DePuy Orthopaedics, Inc, tri-fold brochure, (2009), 2 pgs.
"Vanguard Complete Knee System", Biomet Othopedics, Vanguard, System Summary, (2011), 8 pgs.
"Vanguard® PFR Partial Knee Patellofemoral Replacement System", Surgical Technique, Biomet Orthopaedics,, (Aug. 31, 2010), 1-25.
"What is Subchondroplasty", [Online]. Retrieved from the Internet: <http://www.subchondroplasty.com/about subchondroplasty/what is subchondroplasty.>, (Jul. 1, 2013), 2 pgs.
"Zimmer® UniSpacer® Knee System", Zimmer, Inc., (2005), 4 pgs.
Birnbaum, Klaus M. D, "Computer-Assisted Orthopedic Surgery With Individual Templates and Comparison to Conventional Method", SPINE vol. 26, No. 4, Lippincott Williams & Wilkins, Inc., (2001), 365-370.
Botha, Charl P, "Technical Report: DeVIDE—The Delft Visualisation and Image processing Development Environment", (May 31, 2006), 1-49.
Cohen, Zohara A, et al., "Knee cartilage topography, thickness, and contact areas from MRI: in-vitro calibration and in-vivo measurements", Journal of the OsteoArthritis Research Society International. Osteoarthritis and Cartilage, vol. 7; No. 1, (1999), 95-109.
Deakon, "Posterior Cruciate Ligament Reconstruction Technique Using the Modular ACL/PCL Guide Rationale and Surgical Technique", Arthrotek®, a Biomet Company, (2003), 6 pgs.
Eckhoff, Donald G, et al., "Three-Dimensional Mechanics, Kinematics, and Morphology of the Knee Viewed in Virtual Reality", The Journal of Bone & Joint Surgery, vol. 81, (Dec. 4, 2005), 71-80.
Farr, J, et al., "Anteromedial Tibial Tubercle Osteotomy (Fulkerson Osteotomy)", Re-print from V. Sanchis-Alfonso (ed), Anterior Knee Pain and patellar Instability, DOI: 10.1007/978-0-85729-507-1_40,© Springer-Verlag London Limited, (2011), 9 pgs.
Farr, J, et al., "Surgical Technique for Anteromedialization of the Tibial Tubercle with the Tracker™ AMZ Guide System", Sports Medicine and Arthroscopy Review, vol. 2, No. 3, (1994), 12 pgs.
Fortin, Thomas, et al., "Precise Dental Implant Placement in Bone Using Surgical Guides in Conjunction with Medical Imaging Techniques", Journal of Oral Implantology, Clinical, vol. 26, No, 4, (2000), 300-303.
Friedman, R J, et al., "The Use of Computerized Tomography in the Measurement of Glenoid Version", Journal of Bone & Joint Surgery Am. (JBJS) 1992;74, (Aug. 1992), 1032-1037.
Genant, H K, et al., "Advanced CT bone imaging in osteoporosis", Rheumatology, 47, (2008), 8 pgs.
Guldberg, et al., "3D Imaging of Tissue Integration with Porous Biomaterials", Biomaterials, 29, (Oct. 2008), 3757-3761.

(56) References Cited

OTHER PUBLICATIONS

Haaker, R G, et al., "Minimal-invasive navigiert implantierte unikondylare Knieendoprothese", Orthopade 2006 35: Spinger Medizin Verlag, (Sep. 13, 2006), 1073-1079.
Hafez, M A, et al., "Computer-assisted Total Knee Arthroplasty Using Patient-specific Templating", Clinical Orthopaedics and Related Research, No. 444 Lippincott Williams & Wilkins, (2006), 184-192.
Hajan, Eric, "Computer-Assisted Orthopaedic Sugery, A New Paradigm", Techniques in Orthopaedics® vol. 18, No. 2, (2003), 221-229.
Hutmacher, Dietmar W, "Scaffolds in tissue engineering bone and cartilage", Biomaterials, 21(24), (2000), 2529-2543.
Kaus, Michael R, "Automated Segmentation of MR Images of Brain Tumors", Radiology, vol. 218, No. 2,, (2001), 586-591.
Kelly, Todd C, "Role of Navigation in Total Hip Arthroplasty", The Journal of Bone & Joint Surgery(2009) vol. 91-A, Supplement 1, (2009), 153-8.
Klein, M, "Robot assisted insertion of craniofacial implants—clinical experience", CARS 2001, Elsevier Science B.V., (2001), 133-138.
Lombardi, Adolph, et al., "Patient-Specific Approach in Total Knee Arthroplasty", Knee Orthopedics, ORTHOSuperSite, [Online]. Retrieved from the Internet: <http://www.orthosupersite.com/view.aspx?rid=31419,>, (Sep. 1, 2008), 5 pgs.
Lynch, John A, et al., "Cartilage segmentation of 3D MRI scans of the osteoarthritic knee combining user knowledge and active contours", Medical Imaging 2000: Image Processing SPIE vol. 3979, (2000), 925-935.
Murphy, S B, et al., "The Hip Sextant: Navigation of Acetabular Component Orientation Using a Mechanical Instrument", (2009), 1 pg.
Nicholls, Paul M. D, "Trauma Grand Rounds PMI (Patient-Matched Implants)", Biomet Orthopedics, Inc.,, (Feb. 29, 2000), 1 pg.
Overhoff, H M, et al., "Total Knee Arthroplasty: Coordinate System Definition and Planning based on 3-D Ultrasound Image Volumes", CARS 2001, Elsevier Science B.V., (2001), 283-288.
Patsch, J M, et al., "Noninvasive imaging of bone microarchitecture", Annals of the NY Academy of Sciences, (2011), 77-87.
Portheine, F, "CT-basierte Planung and DISOS-Schablonennavigation in der Kniegelenkendoprothetik", Navigation und Robotic in der Gelenk—und Wirbelsaulenchiruqie, Kapitel 32, Springer Verlag, (2003), 262-269.
Portheine, F, et al., "Entwicklung eines klinischen Demonstrators fur die computerunterstutzte Orthopadische Chirurgie mit CT-Bildbasierten Individualschablonen, Bildverarbeitung fur die Medizin", English version: FIP ID 752773, (1998), 5 pgs.
Portheine, K, "Development of a clinical demonstrator for computer assisted orthopedic surgery with CT-image based individual templates", Computer Assisted Radiology and Surgery Elsevier Science B.V., English Version of FIP ID 752770, (1997), 944-949.
Radermacher, K, et al., "Computer Integrated Orthopaedic Surgery: Connection of Planning and Execution in Surgical Intervention", Computer-integrated surgery: technology and clinical applications, (1996), 451-463.
Radermacher, K, et al., "CT Image-Based Planning and Execution of Interventions in Orthopedic Surgery Using Individual Templates, Experimental Results and Aspects of Clinical Applications", Computer Assisted Orthopedic Surgery (CAOS), Hogrefe & Huber Publishers, (1995), 42-52.
Radermacher, K, et al., "Image Guided Orthopedic Surgery Using Individual Templates", Springer Berlin/Heidelberg, CVRMed-MRCAS'97, vol. 1205, (1997), 606-615.
Radermacher, K, et al., "Technique for Better Execution of CT Scan Planned Orthopedic Surgery on Bone Structures", British Library—"The world's knowledge" 2nd Congress of ISCAS Conference, (Jun. 1995), 933-938.
Radermacher, Klaus, et al., "Computer Assisted Orthopaedic Surgery with Image Based Individual Templates", Clinical Orthopaedics and Related Research No. 354, Lippincott Williams & Wilkins, (Sep. 1998), 28-38.
Sharp, Michael S, "Patient-Specific, Resurfacing Bi-Compartmental Arthruroplasty Futuretech", Orthopaedic Product News, (Apr. 2008), 12-15.
Sisto, Domenick J, et al., "Custome Patellofemoral Arthroplasty of the Knee Surgical Technique", Journal of Bone and Joint Surgery, vol. 89-A, (2006), 214-225.
Slamin, John, et al., "Do You Have This Implant in My Size?", MDT Medical Design Technology, [Online]. Retrieved from the Internet: <http://www.mdtmag.com/scripts/ShowPR.asp?PUBCODE=046&ACCT=0007796& ISSUE...>, (Jul. 31, 2008), 3 pgs.
Steinwachs, Matthias Reinhard, "Cartilage Repair—Autologous Chondrocyte Transplantation and Autologous Matrix-induced Chondrogenesis", European Musculoskeletal Review, (2006), 65-68.
Subburaj, K, et al., "Automated 3D Geometric Reasoning in Computer Assisted Joint Reconstructive Surgery", IEEE International Conference on Automation Science and Engineering, (2009), 367-372.
Thoma, W, et al., "Endoprothetischen Versorgung des Kniegelenks auf der Basis eines 3D-computertomographischen Subtraktionverfahrens", Topic: Computer-aided orthopedic surgery. Orthopedist 2000 29: Springer Verlag W/ Original German Document, (2000), 641-644.
Tripp, et al., "A Nondestructive Prescreening Method for Bone Collagen Content Using Micro-Computed Tomography", Radiocarbon, vol. 52, (2010), 612-619.
"European Application Serial No. 15775589.3, Response filed Dec. 19, 2017 to Communication pursuant to Rules 161(1) and 162 EPC dated Jun. 9, 2017", 14 pgs.

\* cited by examiner

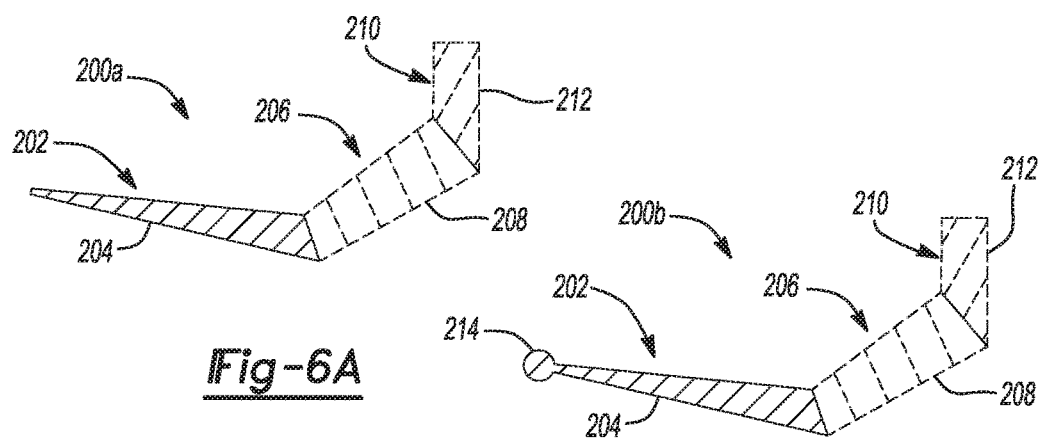
Fig-6A
Fig-6B
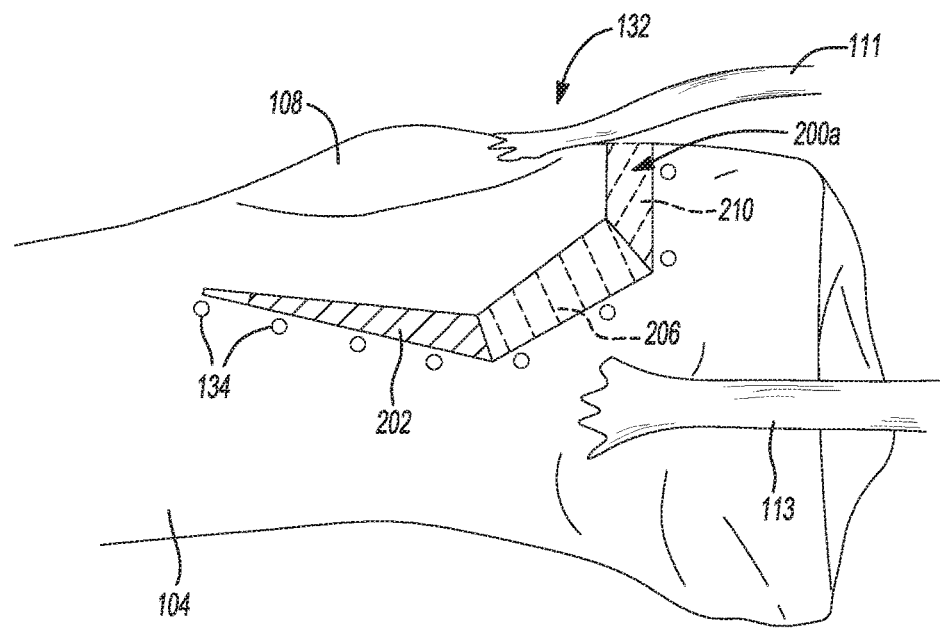
Fig-7

TIBIAL TUBERCLE OSTEOTOMY

RELATED APPLICATIONS

This application is a divisional application and claims the benefit of priority to U.S. application Ser. No. 14/500,019, filed Sep. 29, 2014, the content of which is incorporated herein by reference in its entirety.

BACKGROUND

This section provides background information related to the present disclosure which is not necessarily prior art.

A tibial tubercle osteotomy is a surgical procedure which is performed to treat patellofemoral conditions, such as patellar instability, patellofemoral pain and chondrosis, and osteoarthritis. Such an osteotomy is typically performed when nonoperative measures, such as physical therapy, have failed. During a tibial tubercle osteotomy an incision is made in the anterior of a patient's leg just inferior to the patella, and a proximal and anterior portion of a tibia is partially resected to generate a tubercle flap. The tubercle flap is then repositioned in anterior and medial-lateral directions and held in place with screws. Typically, a tibial tubercle osteotomy results in anteromedialization (AMZ) of the tubercle. This repositioning alters the position of the patella in a patient to remove a pain-causing load, resulting in alleviation of a patellofemoral condition characterized by malalignment of the patella relative to asymptomatic individuals.

Many tibial tubercle osteotomies are performed with the aid of commercially available osteotomy systems. However, these systems generally comprise multiple units that are complicated to use. Moreover, the commercially available systems are mass produced, and are not tailored to a specific patient's anatomy. Therefore, there remains a need to develop new guide systems that are easier to use than currently available systems, and that are custom manufactured to match the anatomy of a specific patient.

SUMMARY

This section provides a general summary of the disclosure, and is not a comprehensive disclosure of its full scope or all of its features.

The present teachings provide a patient-specific guide for a tibial osteotomy. The guide includes a guide body defining a portion with a bone-engaging surface that conforms as a negative surface to a corresponding surface of a specific patient's tibia, and a guide portion that guides a surgical instrument to a specific location on the specific patient's tibia, wherein the bone-engaging surface and guide portion are configured during a pre-operative planning stage.

The present teachings also provide a patient-specific guide for a tibial osteotomy that includes a guide body defining a portion with a bone-engaging surface configured during a pre-operative planning stage of a tibial osteotomy to conform as a negative surface to a corresponding surface of a specific patient's tibia; and a plurality of apertures positioned in a straight line that defines a predetermined angle relative to a proximal-distal axis of the specific patient's tibia that is selected during the pre-operative planning stage of the tibial osteotomy. The plurality of apertures are configured to guide the insertion of a plurality of pins into the tibial. The plurality of apertures have a diameter that is larger than the diameter of the pins, which allows for the guide to be removed while leaving the pins in the tibia. The pins are used as a saw guide for resecting the specific-patient's tibia.

The present teachings further provide for a patient-specific guide for a tibial osteotomy that includes a guide body that defines: (a) a portion with a bone-engaging surface, wherein the bone-engaging surface is configured during a pre-operative planning stage of a tibial osteotomy to conform as a negative surface to a corresponding surface of a specific patient's tibia; (b) a first planar slot oriented at a first predetermined angle and at a first predetermined position relative to a proximal-distal axis of the specific patient's tibia that is selected during the pre-operative planning stage of the tibial osteotomy; (c) a second planar slot oriented at a second predetermined angle and at a second predetermined position relative to the proximal-distal axis of the specific patient's tibia that is selected during the pre-operative planning stage of the tibial osteotomy; and (d) a plurality of apertures. The plurality of apertures are configured to accept pins for removeably anchoring the guide to the specific patient's tibia.

Additionally, the present teachings provide a method for performing a tibial tubercle osteotomy on a patient's tibia. The method includes positioning a patient-specific guide on the patient's tibia, wherein the guide comprises a guide body defining a portion with a bone-engaging surface configured during a pre-operative planning stage of a tibial osteotomy to conform as a negative surface to a corresponding surface of the patient's tibia, and a plurality of apertures; inserting a plurality of pins through the apertures and into the patient's tibia; removing the guide; and resecting the tibia by using the pins inserted into the tibia as a saw guide and sawing the tibia adjacent to the pins from pin to pin to generate a tubercle flap adjacent to a resected surface of the tibia. The method also includes repositioning the tubercle flap in an anterior direction or in both anterior and medial-lateral directions to form a gap between the tubercle flap and the resected surface of the tibia; and implanting a wedge in the gap, wherein the wedge has a predetermined shape configured during the pre-operative planning stage and wherein the wedge is composed of a material that promotes bone in-growth.

Further, the present teachings provide a method for performing a tibial tubercle osteotomy on a patient's tibia. The method includes positioning a patient-specific guide on the patient's tibia, wherein the guide includes: (i) a portion with a bone-engaging surface, wherein the bone-engaging surface is configured during a pre-operative planning stage of a tibial osteotomy to conform as a negative surface to a corresponding surface of a specific patient's tibia; (ii) a first planar slot oriented at a first predetermined angle and at a first predetermined position relative to a proximal-distal axis of the specific patient's tibia that is selected during the pre-operative planning stage of the tibial osteotomy, wherein the first planar slot defined by the guide body has a distal end and a proximal end, and wherein the guide body further defines a circular slot in communication with the first distal end; (iii) a second planar slot oriented at a second predetermined angle and at a second predetermined position relative to the proximal-distal axis of the specific patient's tibia that is selected during the pre-operative planning stage of the tibial osteotomy; and (iv) a plurality of apertures. The method also includes anchoring the guide to the patient's tibia by inserting pins through the apertures; inserting a drill bit through the circular slot and drilling a hole through the tibia; inserting a saw blade through the first slot and resecting a first cut from the hole to the proximal end; inserting the saw blade through the second slot and resecting a second cut; removing the pins and the guide; and further resecting the tibia to connect the first cut and the second cut, and to connect the second cut to a surface of the tibia to form a tubercle flap adjacent to a resected surface of the tibia.

The present teachings additionally provide a surgical kit that includes a patient-specific guide having a guide body defining a portion with a bone-engaging surface that conforms as a negative surface to a corresponding surface of a specific patient's tibia, and a guide portion that guides a surgical instrument to a specific location on the specific patient's tibia, wherein the bone-engaging surface and guide portion are configured during a pre-operative planning stage; a patient-specific implantable wedge with a predetermined shape, wherein the wedge is configured during the pre-operative planning stage; and a plurality of pins.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 6A is a schematic illustration of a first patient-specific implant;

FIG. 6B is a schematic illustration of a second patient-specific implant;

FIG. 7 is a schematic illustration of the patient-specific implant inserted into a gap generated in a tibia with the use of the first patient-specific guide;

Corresponding reference numerals indicate corresponding parts throughout the several views of the drawings.

DETAILED DESCRIPTION

Figure 1:
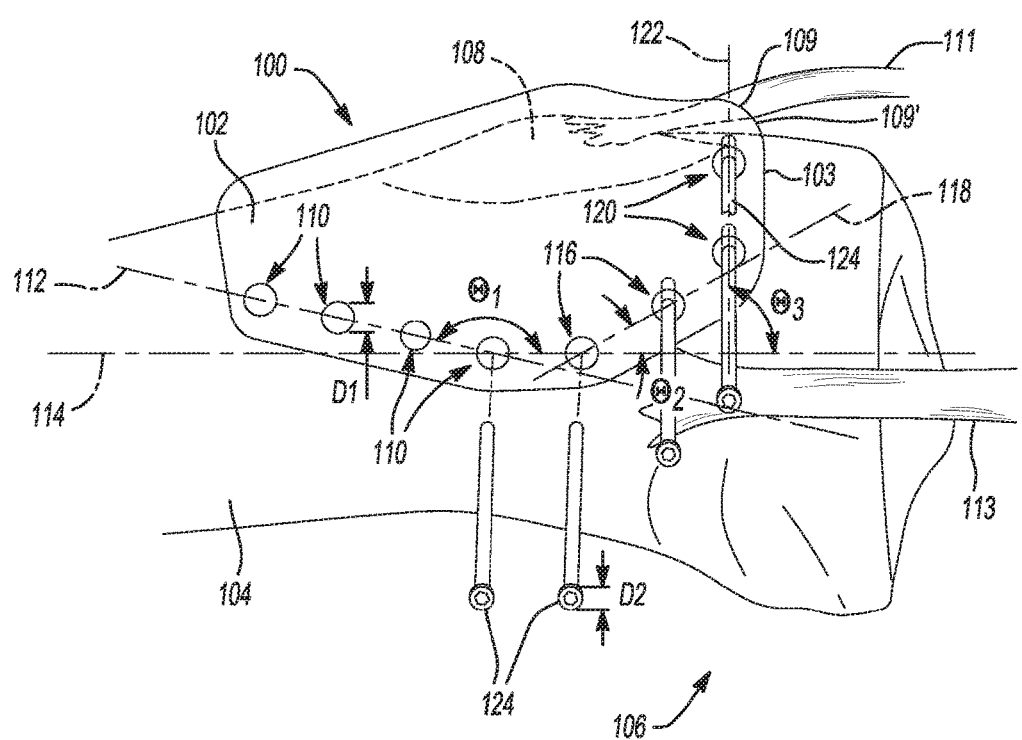
FIG. 1 is a schematic illustration of a first patient-specific guide positioned relative to a tibia.

Example embodiments will now be described more fully with reference to the accompanying drawings.

The present teachings generally provide patient-specific tibial tubercle osteotomy guides that include a guide body defining a portion with a bone-engaging surface that conforms as a negative surface to a corresponding surface of a specific patient's tibia about the patient's tibial tubercle, and a guide portion that guides a surgical instrument to a specific location on the specific patient's tibia, wherein the bone-engaging surface and guide portion are configured during a pre-operative planning stage, in which a medical professional determines the location of a tibial tubercle osteotomy and amount of correction needed. In various embodiments, the guide body further defines a soft tissue engaging surface, wherein the soft tissue-engaging surface is configured during the pre-operative planning stage of a tibial osteotomy to conform as a negative surface to a corresponding surface of a specific patient's soft tissue. The soft tissue can be the patient's medial collateral ligament, lateral cruciate ligament, or patellar tendon. In other embodiments, the guide body defines a surface that allows for clearance of soft tissue.

In one embodiment, the guide portion comprises a plurality of apertures defined by the guide body. The plurality of apertures are configured to guide pins to the specific-patient's tibia, wherein the pins are used as a saw guide for resecting the specific-patient's tibia. The plurality of apertures are positioned in three straight lines that define three predetermined angles relative to a proximal-distal axis of the patient's tibia that are selected during the pre-operative planning stage of the tibial osteotomy.

In another embodiment, the guide portion comprises a first planar slot defined by the guide body oriented at a first predetermined angle and at a first predetermined position relative to a proximal-distal axis of the specific patient's tibia that is selected during the pre-operative planning stage of the tibial osteotomy; and a second planar slot defined by the guide body oriented at a second predetermined angle and at a second predetermined position relative to the proximal-distal axis of the specific patient's tibia that is selected during the pre-operative planning stage of the tibial osteotomy. The first planar slot defined by the guide body has a distal end and a proximal end, wherein the guide body further defines a circular slot in communication with the first distal end.

The patient-specific alignment guides can be used either with conventional or patient-specific implant components prepared with computer-assisted image methods. Computer modeling for obtaining three dimensional images of the patient's anatomy using x-ray, MRI or CT scans of the patient's anatomy, the patient specific prosthesis components, and the patient-specific guides can be provided by various CAD programs and/or software available, for example, by Materialise USA, Plymouth, Mich. The guide will allow a surgeon to precisely cut an osteotomy, which ensures that an implant will match the native bone anatomy and provide the proper amount of adjustment.

The patient-specific alignment guides and associated patient-specific implants disclosed herein can be generally formed using computer modeling based on the patient's 3-D anatomic image generated from image scans. The patient-specific alignment guides can have a three-dimensional patient-specific engagement surface that is made to conformingly contact, mate with, and match a three-dimensional image of the patient's bone surface (selectively with or without soft tissue), by the computer methods discussed above. The patient-specific alignment guides can include custom-made guiding formations, such as, for example, guiding bores or guiding apertures, cannulated guiding extensions or receptacles that can be used for supporting or guiding other instruments, such as drill guides, reamers, cutters, and cutting guides or for inserting pins or other fasteners according to a surgeon-approved pre-operative plan.

In various embodiments, the patient-specific alignment guide can include one or more patient-specific cutting guides for receiving and guiding a cutting blade at corresponding patient-specific cutting plane orientations relative to a selected anatomic axis for the specific patient. The patient-specific alignment guides can also include guiding formations for guiding the implantation of patient-specific or off-the-shelf implants associated with the osteotomy procedure, such as implantable wedges and implantable fixation plates. The geometry, shape and orientation of the various features of the patient-specific alignment guide, as well as various patient-specific implants and other patient-specific tools can be determined during the pre-operative planning stage of the procedure in connection with the computer-assisted modeling of the patient's anatomy. During the pre-operative planning stage, patient-specific alignment guides, implants and other tools, can be designed and manufactured for a specific patient with input from a surgeon or other professional associated with the surgical procedure, as described in U.S. Pat. No. 8,632,547, issued on Jan. 21, 2014 to Maxson et al., U.S. Pat. No. 8,241,293, issued on Aug. 14, 2012 to Stone et al., and U.S. application Ser. No. 14/262,105 to Eash, filed on Apr. 25, 2014, all of which are incorporated herein by reference.

In the following discussion, the terms "patient-specific", "custom-made" or "customized" are defined to apply to components, including tools, implants, portions or combinations thereof, which include certain geometric features, including surfaces, curves, or other lines, and which are made to closely conform as mirror-images or negatives of corresponding geometric features of a patient's anatomy during a pre-operative planning stage based on 3-D computer images of the corresponding anatomy reconstructed from image scans of the patient by computer imaging methods. Further, patient-specific guiding features, such as, guiding apertures and guiding slots, or other holes or openings that are included in alignment guides or in implants are defined as features that are made to have positions, orientations, dimensions, shapes and/or define cutting planes specific to the particular patient's anatomy based on the computer-assisted pre-operative plan associated with the patient.

The current technology provides a patient-specific tibial osteotomy guide 100 as shown in FIG. 1. The guide 100 comprises a guide body 102 that defines a portion with a bone-engaging surface 103 configured during a pre-operative planning stage of a tibial osteotomy to conform as a negative surface to a corresponding surface of a specific patient's tibia 104. As shown in FIG. 1, the guide 100 is positioned on the specific patient's tibia 104 about a tubercle 108 on a medial face of the tibia 104. In other embodiments, the guide 100 can be configured to be positioned on a lateral face of the specific patient's tibia 104. The bone engaging surface 103 is custom made during the preoperative planning stage to match a specific patient's anatomy and allows for placement of the guide 100 at a specific location at a proximal portion 106 of the patient's tibia 104. Typically, the guide 100 is configured to fit on and nest with only one position on the specific patient's tibia 104 at, around, or near the tubercle 108, which is to be repositioned during an osteotomy.

In some embodiments, the guide body 102 also defines a soft tissue-clearing portion 109 that allows for clearance of soft tissue, such as ligaments and tendons. The soft tissue-clearing portion 109 has an outer convex surface and an inner concave surface, wherein the inner concave surface provides a recess for accommodating soft tissue. As shown in FIG. 1, the soft tissue-clearing portion 109 accommodates the patient's patellar tendon 111. However, in various embodiments, the tissue-clearing portion 109 accommodates a medial collateral ligament (MCL) 113 or a lateral cruciate ligament (LCL, not shown). In this regard, the bone-engaging surface 103 mates with and conforms to a specific boney region of the tibia 104, and the patellar soft tissue-clearing portion 109 allows for the guide to simultaneously be placed about the patient's soft tissue, such as the patellar tendon 111. In other embodiments, the guide 100 comprises a plurality of tissue-clearing portions 109 for simultaneously accommodating the LCL and patellar tendon, or MCL and patellar tendon.

In additional embodiments, the guide body 102 further defines a soft tissue engaging surface 109', wherein the soft tissue-engaging surface 109' is configured during the pre-operative planning stage of a tibial osteotomy to conform as a negative surface to a corresponding surface of a specific patient's soft tissue at, around, or near the tubercle 108. The soft tissue can be, for example, the patient's MCL, LCL, or patellar tendon. In various embodiments, the guide 100 comprises a plurality of soft tissue engaging surfaces 109' for simultaneously accommodating the LCL and patellar tendon, or MCL and patellar tendon. In other embodiments, the guide 100 has both a soft tissue-clearing portion 109 and a soft tissue engaging surface 109'.

The guide body 102 further defines a first plurality of apertures 110 positioned along a first straight line 112 that defines a first predetermined angle $\theta_1$ relative to a proximal-distal axis 114 of the specific patient's tibia 104. The first straight line 112 is selected during the pre-operative planning stage of the tibial osteotomy. In many embodiments, a second plurality of apertures 116 is positioned along a second straight line 118 that defines a second predetermined angle $\theta_2$ relative to the proximal-distal axis 114 of the specific patient's tibia 104 that is selected during the pre-operative planning stage of the tibial osteotomy, wherein the second line 118 intersects the first line 112. In yet other embodiments, a third plurality of apertures 120 is positioned along a third straight line 122 that defines a third predetermined angle $\theta_3$ relative to the proximal-distal axis 114 of the specific patient's tibia 104 that is selected during the pre-operative planning stage of the tibial osteotomy, wherein the third line 122 intersects the second line 118.

Figure 3:
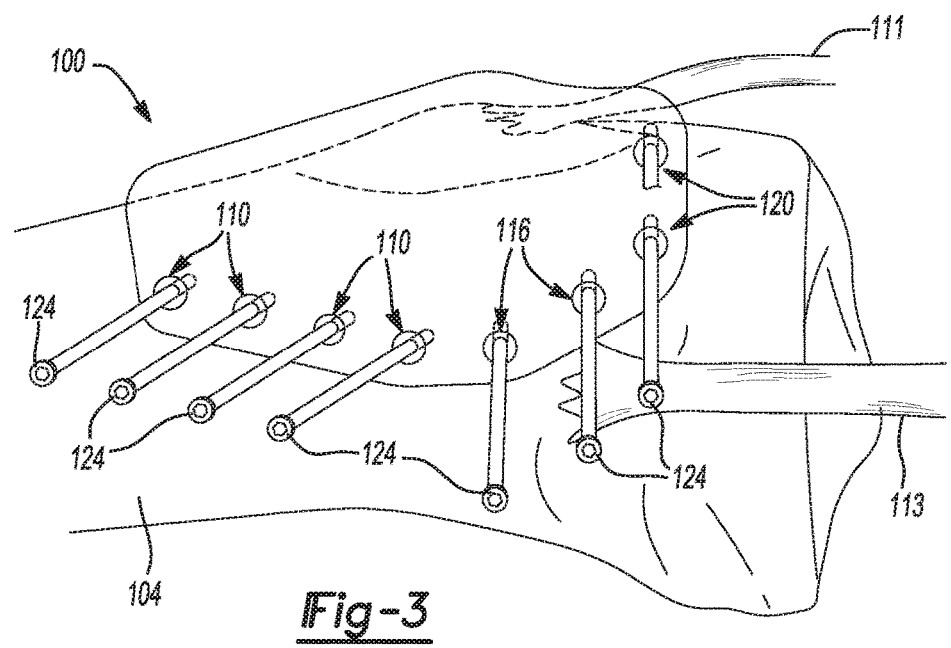
FIG. 3 is a schematic illustration of the first patient-specific guide positioned relative to the tibia, with pins inserted into the tibia.
Figure 4:
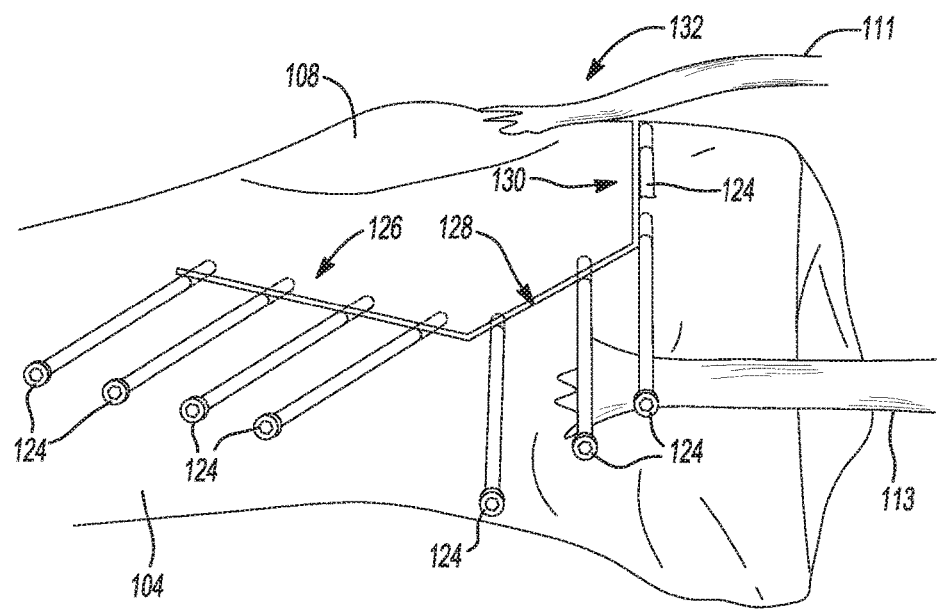
FIG. 4 is a schematic illustration of planes cut through a tibia along the pins positioned with the use of the first patient-specific guide to generate a tubercle flap.

The first, second, and third plurality of apertures 110, 116, 120 are configured to guide a plurality of pins 124 to the tibia 104 for insertion. The plurality of apertures 110, 116, 120 have a diameter $D_1$ and the pins 124 have a diameter $D_2$, wherein $D_1$ is larger than $D_2$. Because the apertures 110, 116, 120 have a larger diameter than the pins 124, the guide 100 can be removed from the tibia 104 by simply sliding the guide 100 off from the implanted pins 124. When the guide 100 is removed, the pins 124 provide a saw guide for resecting planes in the tibia 104 adjacent to the pins 124, from pin 124 to pin 124, to generate a tubercle flap 132 as shown in FIGS. 3, 4, and 6. Accordingly, the saw guide is adjacent to the pins 124 and matches the lines 112, 118, 122, configured during the preoperative planning stage. In other words, the pins 124 give visual indicia to a physician for making three intersecting planar cuts through the tibia 104.

Figure 2:
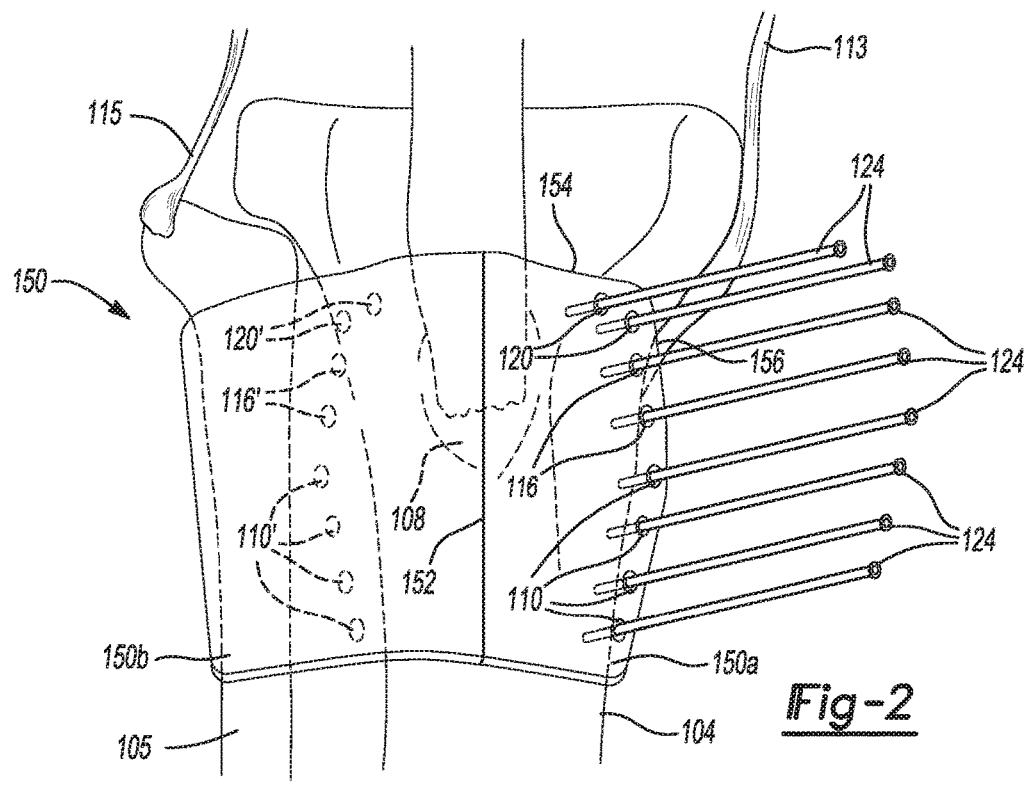
FIG. 2 is a schematic illustration of a second embodiment of the first patient-specific guide positioned relative to a tibia.

As shown in FIG. 2, in various embodiments, the present technology provides for a bifurcated patient-specific alignment guide 150 comprising a first guide half 150a removeably coupled to a second guide half 150b at a seam 152. The first half of the bifurcated patient-specific alignment guide 150a has similar features as the alignment guide 100 shown in FIGS. 1 and 3, such as a plurality of apertures 110, 116, 120 for guiding a plurality of pins 124 to the tibia 104. Optionally, the second half of the guide 150b can also have a plurality of apertures 110', 116', and 120' for guiding pins 124 to the tibia 104. The bifurcated guide 150 has at least one bone-engaging surface 154 that nests with and conforms to a boney structure. The boney structure can be a structure on the tibia 104 or on the fibula 105. In other embodiments, the bifurcated guide 150 has at least one soft tissue engaging surface 156 that either nests with and conforms to or provides clearance for at least one soft tissue, such as a soft tissue selected from the group consisting of the patient's MCL 113, LCL 115, patellar tendon 111, and combinations thereof. In yet other embodiments, the bifurcated guide 150 has both at least one bone-engaging surface 154 and at least one soft tissue-engaging surface 156. The second guide half 150b allows for the guide 150 to nest with and conform to more boney structures and/or soft tissue structures than a guide that does not comprise two halves. After the pins 124 have been positioned into the tibia 104, the bifurcated guide 150 can be separated at the seam 152, which permits both the first half 150a and the second half 150b to slide over the pins 124 and away from the tibia 104. With reference to FIG. 6A, the present technology provides a patient-specific implant or wedge 200a that is configured during a pre-operative planning stage of a tibial tubercle osteotomy to be wedged in a gap generated from a resection guided by the patient-specific guide 100 to maintain the position of a patient's tibial tubercle 108 relative to the tibia 104. The patient-specific implant 200 comprises a first portion 202 that has a first surface 204 that corresponds to the line 112 shown in FIG. 1. Because the first surface 204 corresponds to the line 112, the implant 200a is custom designed to fit in a gap generated from a resection guided by the patient specific guide 100. In some embodiments, the implant 200a further comprises an optional second portion 206 that has a second surface 208 that corresponds to the line 118 shown in FIG. 1. Because the first surface 204 corresponds to the line 112, and because the second surface 208 corresponds to the line 118, the implant 200a with first and second portions 202, 206 is custom designed to fit in a gap generated from a resection guided by the patient specific guide 100. In yet other embodiments, the implant 200a further comprises an optional third portion 210 that has a third surface 212 that corresponds to the line 122 shown in FIG. 1. Because the first surface 204 corresponds to the line 112, the second surface 208 corresponds to the line 118, and the third surface 212 corresponds to the line 122, the implant 200a with first, second and third portions 202, 206, 210 is custom designed to fit in a gap generated from a resection guide by the patient specific guide 100. The patient-specific implant can be composed of a material that promotes bone in-growth. FIG. 6B is a second patient-specific implant 200b that is similar to the implant 200a. However, the second implant 200b further comprises a substantially spherical portion 214 coupled to the first portion 202. The spherical portion 214 is designed to fit in a hinge bore or a stress relief hole, as described further below.

With reference to FIG. 1, the present technology provides a method for performing a tibial tubercle osteotomy on a patient's tibia 104 with the patient-specific alignment guide 100. The method comprises positioning the patient-specific guide 100 on the patient's tibia 104 at, near, or around the tubercle 108, wherein the guide 100 comprises a guide body 102 defining a portion with a bone-engaging surface configured during a pre-operative planning stage of a tibial osteotomy to conform as a negative surface to a corresponding surface of the patient's tibia 104, and a first plurality of apertures 110 along line 112. As described above, in some embodiments, the guide body 102 further defines a second plurality of apertures 116 along line 118 and a third plurality of apertures 120 along line 122. Accordingly, the apertures 110, 116, 120 are positioned in three intersecting straight lines 112, 118, 122 that define three predetermined angles 81, 82, 83 relative to a proximal-distal axis 114 of the patient's tibia 104 that are selected during the pre-operative planning stage of the tibial osteotomy. The guide 100 is custom made to mate with and conform to the specific patient's tibia 104, at a proximal end 106 at or near the tubercle 108. The method also includes inserting a plurality of pins 124 through the first plurality of apertures 110, and into the optional second and third plurality of apertures 116, 120, and into the patient's tibia 104. FIG. 3 shows the guide 100 positioned on the specific-patient's tibia 104, wherein pins 124 10 have been placed through the first, second, and third plurality of apertures 110, 116, 120 and into the tibia 104.

After the pins 124 have been inserted into the tibia 104, the method comprises removing the guide 100 from the tibia 104. Because the diameter $D_1$ of the apertures 110, 116, 120 is larger than the diameter $D_2$ of the pins 124, the guide 100 can be removed by simply sliding the guide 100 over the pines 124.

With reference to FIG. 4, when the pins 124 are inserted into the tibia 104, and the guide 100 has been removed, the method comprises resecting a first plane 126 into the tibia 104 adjacent to the pins 124 that are in line with the first line 112. Optionally, a bore, such as a hinge bore or a stress relief hole, can be drilled into the tibia 104 adjacent to the most distal pin 124, wherein the first plane 126 is resected from the bore to the most proximal pin 124 adjacent to the first line 112. Therefore, the pins 124 provide a saw guide for resecting the first plane 126 in the tibia 104 adjacent to the pins 124, from pin 124 to pin 124. Likewise, resecting further comprises resecting a second plane 128 into the tibia 104 adjacent to the pins 124 that are in line with the second line 118, and resecting a third plane 130 into the tibia 104 adjacent to the pins 124 that are in line with the third line 122. Resecting is performed, for example, with an oscillating saw. When all three planes 126, 128, 130 have been resected, a tubercle flap 132 is generated. Accordingly, the planes 126, 128, 130 resected into the tibia 104 are adjacent to and match the lines 112, 118, 122 configured during the preoperative planning stage.

Figure 5:
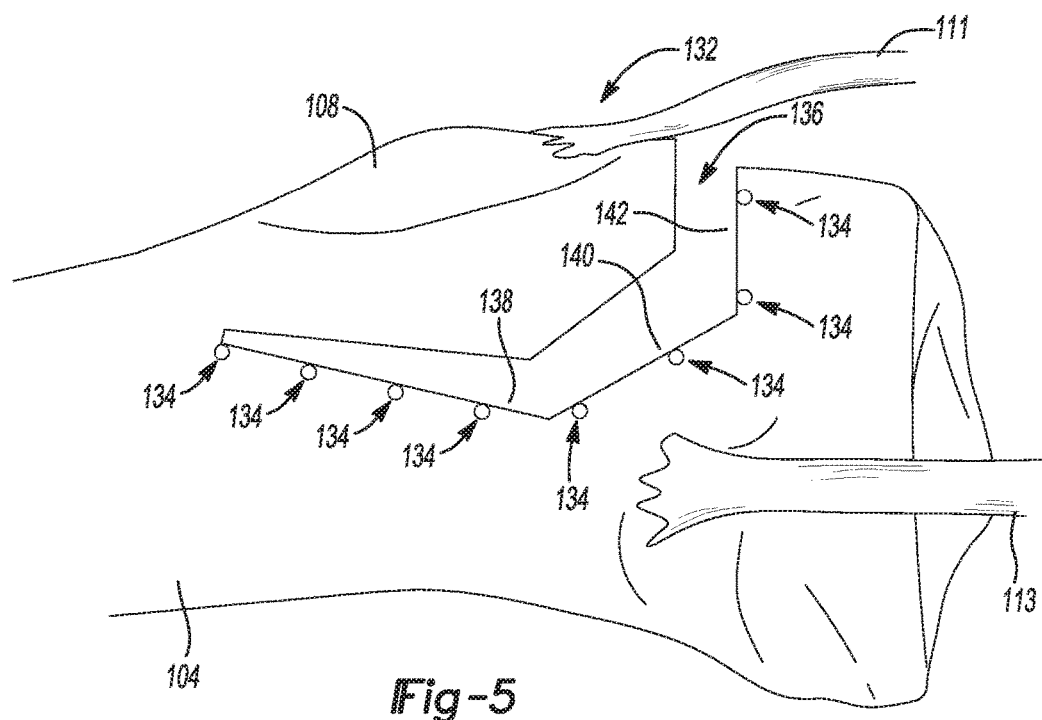
FIG. 5 is a schematic illustration of a repositioned tubercle flap generated with the use of the first patient-specific guide.

As shown in FIG. 5, after resecting, the method comprises removing the pins 124 from the tibia 104. When the pins 124 are removed, holes 134 remain in the tibia 104. After the tubercle flap 132 has been generated, the method comprises repositioning the tubercle flap 132 in an anterior direction or in both anterior and medial-lateral directions to form a gap 136 between the tubercle flap 132 and the and three resected surfaces 138, 140, 142 of the tibia 138. Repositioning the tubercle flap 132 alters the position of the patient's patella to remove a pain-causing load and results in alleviation of a patellofemoral condition characterized by malalignment of the patella relative to asymptomatic individuals. The tubercle flap 132 is repositioned to a location predetermined during the pre-operative planning stage. After repositioning the tubercle flap 132 the method comprises implanting or positioning a patient specific implant or wedge 200a implant gap 136, as shown in FIGS. 6A and 7. In embodiments where a hinge bore or a stress relief is drilled into the tibia 104, the implant or wedge 200b shown in FIG. 6B is utilized. As described above, the patient-specific implant 200a has a predetermined shape configured during the pre-operative planning stage. The implant 200a comprises a first portion 202, and optionally a second portion 206 or a second 206 and third portion 210. In some embodiments, the patient-specific implant is composes of a material that promote bone in-growth. In an alternative method, the implant is an off-the-shelf, i.e., non-patient-specific, implantable wedge. Optionally, the method comprises securing the tubercle flap 132 by driving a screw through the tubercle flap 132 and the wedge 200a, and into the tibia 104 through one of the resected surfaces 138, 140, 142. The wedge 200a maintains the position of the repositioned tubercle flap 132 and prevents the tubercle flap 132 from reverting to its original location.

Figure 8:
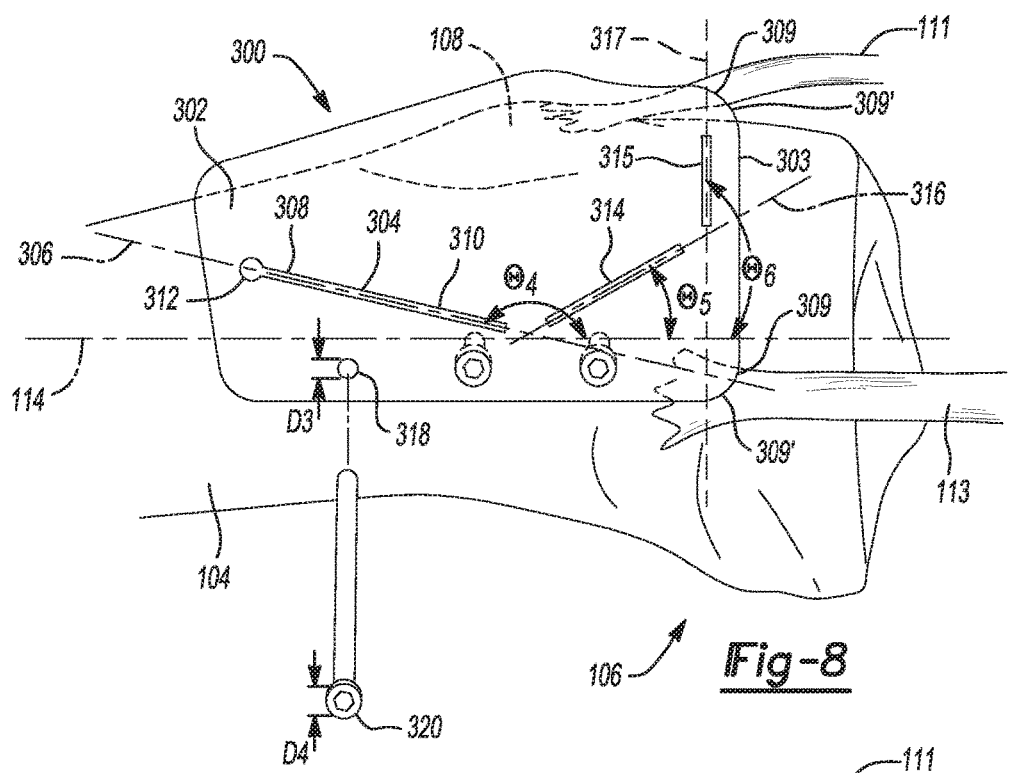
FIG. 8 is a schematic illustration of a second patient-specific guide positioned relative to a tibia.

The current technology provides another patient-specific tibial osteotomy guide 300 as shown in FIG. 8. The guide 300 comprises a guide body 302 that defines a portion with a bone-engaging surface 303 configured during a pre-operative planning stage of a tibial osteotomy to conform as a negative surface to a corresponding surface of a specific patient's tibia 104. As shown in FIG. 8, the guide 300 is positioned on the specific patient's tibia 104 about a tubercle 108 on a medial face of the tibia 104. In other embodiments, the guide 300 can be configured to be positioned on a lateral face of the specific patient's tibia 104. The bone engaging surface 303 is custom made during the preoperative planning stage to match a specific patient's anatomy and allows for placement of the guide 300 at a specific location, and in only one position, at a proximal portion 106 of the patient's tibia 104. Typically, the guide 300 is configured to fit on a specific patient's tibia 104 at, around, or near the tubercle 108, which is to be repositioned during an osteotomy.

In some embodiments, the guide body 302 also defines a soft tissue-clearing portion 309 that allows for clearance of soft tissue, such as ligaments and tendons. The soft tissue-clearing portion 309 has an outer convex surface and an inner concave surface, wherein the inner concave surface provides a recess for accommodating soft tissue. As shown in FIG. 8, the soft tissue-clearing portion 309 accommodates the patient's patellar tendon 111. However, in various embodiments, the tissue-clearing portion 309 accommodates a medial collateral ligament (MCL) 113 or a lateral cruciate ligament (LCL, not shown). In this regard, the bone-engaging surface 303 mates with and conforms to a specific boney region of the tibia 104, and the patellar soft tissue-clearing portion 309 allows for the guide to simultaneously be placed about the patient's soft tissue, such as the patellar tendon 111. In other embodiments, the guide 300 comprises a plurality of tissue-clearing portions 309 for simultaneously accommodating the LCL and patellar tendon, or MCL and patellar tendon.

In additional embodiments, the guide body 302 further defines a soft tissue engaging surface 309', wherein the soft tissue-engaging surface 309' is configured during the pre-operative planning stage of a tibial osteotomy to conform as a negative surface to a corresponding surface of a specific patient's soft tissue at, around, or near the tubercle 108. The soft tissue can be, for example, the patient's MCL, LCL, or patellar tendon. In various embodiments, the guide 300 comprises a plurality of soft tissue engaging surfaces 309' for simultaneously accommodating the LCL and patellar tendon, or MCL and patellar tendon. In other embodiments, the guide 300 has both a soft tissue-clearing portion 309 and a soft tissue engaging surface 309'.

The guide body 302 further defines a first planar slot 304 positioned along a fourth straight line 306 that defines a fourth predetermined angle 84 relative to a proximal-distal axis 114 of the specific patient's tibia 104. The fourth straight line 306 is selected during the pre-operative planning stage of the tibial osteotomy. Therefore, the first planar slot 304 is oriented at a fourth predetermined angle 84 and at a first predetermined position relative to a proximal-distal axis 114 of the specific patient's tibia 104 that is selected during the pre-operative planning stage of the tibial osteotomy. The first planar slot 304 defined by the guide body 302 has a distal end 308 and a proximal end 310, wherein the guide body 302 further defines a circular slot 312 in communication with the first distal end 308.

Additionally, the guide body 302 defines a second planar slot 314 positioned along a fifth straight line 316 that defines a fifth predetermined angle $\theta_5$ relative to a proximal-distal axis 114 of the specific patient's tibia 104. The fifth straight line 316 is selected during the pre-operative planning stage of the tibial osteotomy. Therefore, the second planar slot 314 is oriented at a fifth predetermined angle $\theta_5$ and at a second predetermined position relative to a proximal-distal axis 114 of the specific patient's tibia 104 that is selected during the pre-operative planning stage of the tibial osteotomy Additionally, the guide body 302 defines a third planar slot 315 positioned along a fifth straight line 317 that defines a sixth predetermined angle $\theta_6$ relative to a proximal-distal axis 114 of the specific patient's tibia 104. The sixth straight line 317 is selected during the pre-operative planning stage of the tibial osteotomy. Therefore, the third planar slot 315 is oriented at a sixth predetermined angle $\theta_6$ and at a third predetermined position relative to a proximal-distal axis 114 of the specific patient's tibia 104 that is selected during the pre-operative planning stage of the tibial osteotomy The guide body 302 of the patient specific guide 300 also defines a plurality of apertures 318 for removeably anchoring the guide 300 to the specific patient's tibia 104. The apertures have a diameter $D_3$ and the pins have a diameter $D_4$, wherein $D_3$ is smaller than $D_4$. Because the apertures 318 have a smaller diameter than the pins 320, the guide 300 can be attached to the tibia 104 by way inserting the pins 320 through the apertures 318 and into the tibia 104. To remove the guide 300 from the tibia 104, the pins 320 must first be removed.

The present technology also provides a method for performing a tibial tubercle osteotomy on a patient's tibia with the use of the patient-specific guide 300. As shown in FIG. 8, the method comprises anchoring the guide 300 to the patient's tibia 104 by inserting pins 320 through the apertures 318 and into the tibia 104. When the guide 300 is anchored in place, the method comprises inserting a drill bit through the circular slot 312 and drilling a circular hinge bore or stress relief hole 322 through the tibia 104.

Figure 9:
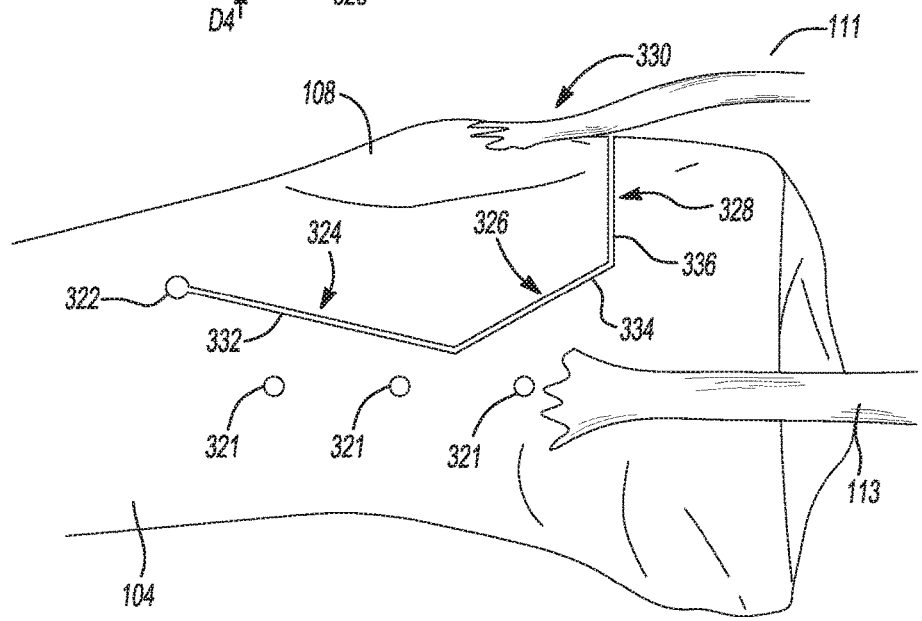
FIG. 9 is a schematic illustration of planes cut through a tibia with the use of the second patient-specific guide to generate a tubercle flap.

After drilling, the method comprises inserting a saw blade through the first slot 304 and resecting a first plane 324 from the bore 322 to the proximal end 310 of the first slot 304. Likewise, the method comprises inserting the saw blade through the second slot 314 and resecting a second plane 326 and inserting the saw blade through the third slot 315 and resecting a third plane 328. Resecting can be performed, for example, with an oscillating saw. After the planes 324, 326, 328 have been resected through the tibia 104 via the slots 304, 314, 315 in the guide 300, the method comprises removing the pins 320 from the tibia 104, which exposes pin holes 321, and subsequently removing the guide 300. As shown in FIG. 9, after the guide 300 has been removed, the method comprises resecting the tibia 104 to connect the first plane 324 to the second plane 326, the second plane 326 to the third plane 328, and the third plane 328 to an anterior surface of the tibia 104 proximal to the tubercle 108 to form a tubercle flap 330 adjacent to a resected surface of the tibia.

Figure 10:
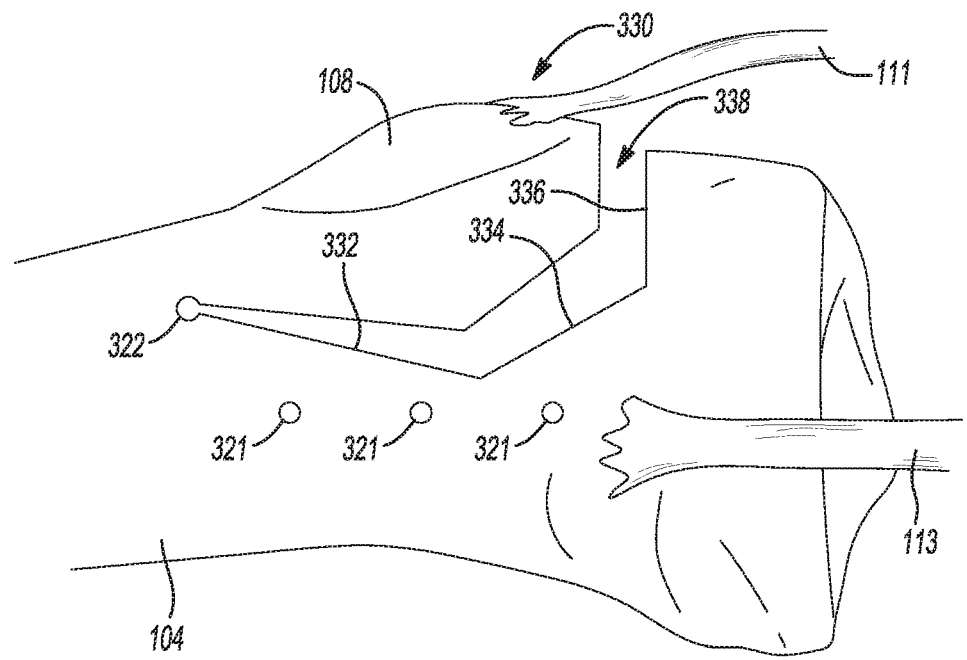
FIG. 10 is a schematic illustration of a repositioned tubercle flap generated with the use of the second patient-specific guide.
Figure 11:
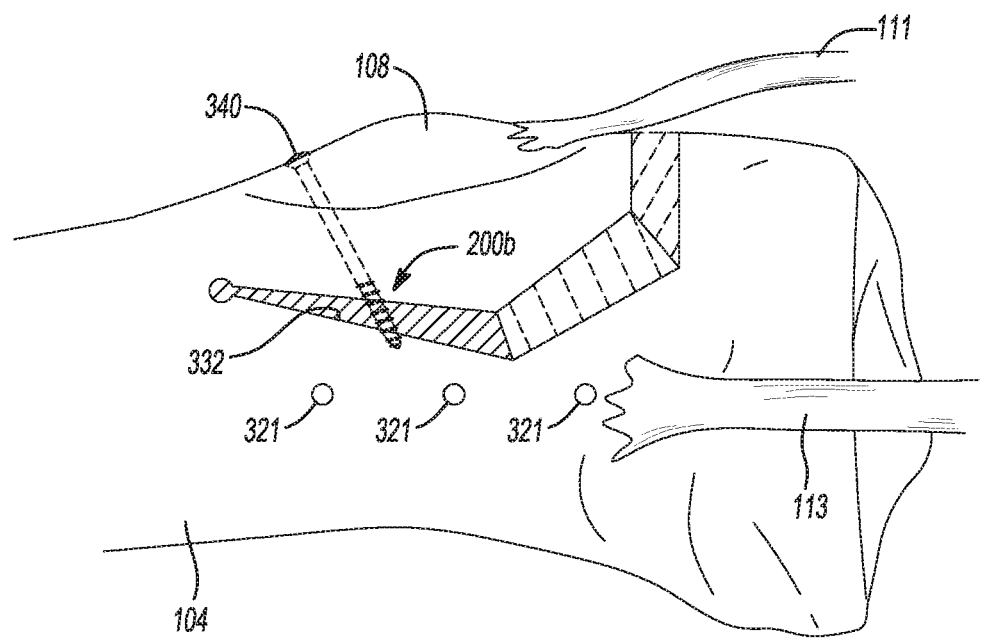
FIG. 11 is a schematic illustration of the patient-specific implant inserted into a gap generated in a tibia with the use of the second patient-specific guide.

As shown in FIG. 10, after the tubercle flap 330 has been generated, the method comprises repositioning the tubercle flap 330 in an anterior direction or in both anterior and medial-lateral directions to form a gap 338 between the tubercle flap 330 and three resected surfaces 332, 334, 336 of the tibia 104. The hinge bore or stress relief hole 322 ensures that repositioning the tubercle flap 330 does not crack or splinter the tibia 104. The tubercle flap 330 is repositioned to a location predetermined during the pre-operative planning stage. Repositioning the tubercle flap 132 alters the position of the patient's patella remove a pain-causing load and results in alleviation of a patellofemoral condition characterized by malalignment of the patella relative to asymptomatic individuals. After repositioning the tubercle flap 330 the method comprises implanting or positioning a patient specific implant or wedge 200a, 200b in gap 338, as shown in FIGS. 6A, 6B, and 11. As described above, the patient-specific implant 200a, 200b has a predetermined shape configured during the preoperative planning stage. The implant 200a, 200b comprises a first portion 202, and optionally a second portion 206 or a second 206 and third portion 210. In some embodiments, the patient-specific implant 200a, 200b is composed of a material that promotes bone in-growth. When the second implant 200b is used, the spherical portion 214 is positioned in the stress relief hole 322. In an alternative method, the implant is an off-the-shelf, i.e., non-patient-specific, implantable wedge. Optionally, the method comprises securing the tubercle flap 330 by driving a screw 340 through the tubercle flap 330 and the wedge 200a, 200b, and into the tibia 104 through one of the resected surface 332. The wedge 200a, 200b maintains the position of the repositioned tubercle flap 330 relative to the tibia 104 and prevents the tubercle flap 330 from reverting to its original location.

The present technology additionally provides for a surgical kit or a system for a tibial osteotomy comprising a patient-specific guide comprising a guide body defining a portion with a bone-engaging surface that conforms as a negative surface to a corresponding surface of a specific patient's tibia, and a guide portion that guides a surgical instrument to a specific location on the specific patient's tibia, wherein the bone-engaging surface and guide portion are configured during a pre-operative planning stage; a patient-specific implantable wedge with a predetermined shape, wherein the wedge is configured during the pre-operative planning stage; and a plurality of pins.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A patient-specific system for a tibial osteotomy, comprising: a patient-specific guide comprising a guide body defining,
    a bone-engaging portion with a bone-engaging surface, wherein the bone-engaging surface is configured during a pre-operative planning stage of a tibial osteotomy to conform as a negative surface to a corresponding surface of a specific patient's tibia at, around, or near the patient's tibial tubercle;
    a first planar slot oriented at a first predetermined angle and at a first predetermined position relative to a proximal-distal axis of the specific patient's tibia that is selected during the pre-operative planning stage of the tibial osteotomy;
    a second planar slot oriented at a second predetermined angle and at a second predetermined position relative to the proximal-distal axis of the specific patient's tibia that is selected during the pre-operative planning stage of the tibial osteotomy; and
    a plurality of apertures.

2. The patient-specific system according to claim 1, wherein the first planar slot defined by the guide body has a distal end and a proximal end, and wherein the guide body further defines a circular slot in communication with the first distal end.

3. The patient-specific system according to claim 1, wherein the plurality of apertures are configured to accept pins for removeably anchoring the guide to the specific patient's tibia at a single location near the patient's tibial tubercle.

4. The patient-specific system according to claim 1, wherein the guide body further defines a soft tissue-engaging surface, wherein the soft tissue-engaging surface is configured during the pre-operative planning stage of a tibial osteotomy to conform as a negative surface to a corresponding surface of a specific patient's soft tissue at or about the tubercle.

5. The patient-specific system according to claim 4, wherein the specific patient's soft tissue is the patient's medial collateral ligament, lateral cruciate ligament, or patellar tendon.

6. The patient-specific system according to claim 1, wherein the guide body further defines a soft tissue-clearing portion comprising an outer convex surface and an inner concave surface, wherein the inner concave surface provides a recess for accommodating the patient's medial collateral ligament, lateral cruciate ligament, or patellar tendon.

7. A patient-specific system for a tibial osteotomy, comprising: a patient-specific guide comprising a guide body defining,
    a bone-engaging portion with a bone-engaging surface, wherein the bone-engaging surface is configured during a pre-operative planning stage of a tibial osteotomy to conform as a negative surface to a corresponding surface of a specific patient's tibia at, around, or near the patient's tibial tubercle;
    a first planar slot oriented at a first predetermined angle and at a first predetermined position relative to a proximal-distal axis of the specific patient's tibia that is selected during the pre-operative planning stage of the tibial osteotomy; and
    a second planar slot oriented at a second predetermined angle and at a second predetermined position relative to the proximal-distal axis of the specific patient's tibia that is selected during the pre-operative planning stage of the tibial osteotomy;

wherein the guide body further defines a soft tissue-engaging surface, wherein the soft tissue-engaging surface is configured during the pre-operative planning stage of a tibial osteotomy to conform as a negative surface to a corresponding surface of a specific patient's soft tissue at or about the tubercle, and wherein the specific patient's soft tissue is the patients medial collateral ligament, lateral cruciate ligament, or patellar tendon.

8. The patient-specific system of claim 7, wherein the first planar slot defined by the guide body has a distal end and a proximal end, and wherein the guide body further defines a circular slot in communication with the first distal end.

9. The patient-specific system according to claim 7, further comprising a plurality of apertures configured to accept pins for removeably anchoring the guide to the specific patient's tibia at a single location near the patient's tibial tubercle.

10. The patient-specific system according to claim 7, wherein the guide body further defines a soft tissue-clearing portion comprising an outer convex surface and an inner concave surface, wherein the inner concave surface provides a recess for accommodating the patient's medial collateral ligament, lateral cruciate ligament, or patellar tendon.

* * * * *